(12) United States Patent
Miller et al.

(10) Patent No.: US 6,572,547 B2
(45) Date of Patent: Jun. 3, 2003

(54) TRANSESOPHAGEAL AND TRANSNASAL, TRANSESOPHAGEAL ULTRASOUND IMAGING SYSTEMS

(75) Inventors: David G. Miller, North Andover, MA (US); Michael Peszynski, Newburyport, MA (US); Heather Beck, Chelmsford, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/919,464

(22) Filed: Jul. 31, 2001

(65) Prior Publication Data

US 2003/0028107 A1 Feb. 6, 2003

(51) Int. Cl.$^7$ ................................................. A61B 8/00
(52) U.S. Cl. ....................................... 600/437; 600/459
(58) Field of Search ................................ 600/437, 443, 600/444, 445, 447, 448, 461, 462, 463, 459, 449

(56) References Cited

U.S. PATENT DOCUMENTS

| | | | |
|---|---|---|---|
| 4,140,022 A | | 2/1979 | Maslak |
| 4,468,747 A | | 8/1984 | Leavitt et al. |
| 4,471,449 A | | 9/1984 | Leavitt et al. |
| 4,543,960 A | | 10/1985 | Harui et al. |
| 4,757,821 A | * | 7/1988 | Snyder ...................... 600/453 |
| 5,181,514 A | | 1/1993 | Solomon et al. |
| 5,195,521 A | | 3/1993 | Melton, Jr. et al. |
| 5,197,037 A | | 3/1993 | Leavitt |
| 5,207,225 A | | 5/1993 | Oaks et al. |
| 5,345,426 A | | 9/1994 | Lipschutz |
| 5,398,691 A | * | 3/1995 | Martin et al. ................ 600/437 |
| 5,402,793 A | | 4/1995 | Gruner et al. |
| 5,469,851 A | | 11/1995 | Lipschutz |
| 5,546,807 A | | 8/1996 | Oxaal et al. |
| 5,771,896 A | | 6/1998 | Sliwa, Jr. et al. |
| 6,066,096 A | | 5/2000 | Smith et al. |
| 6,276,211 B1 | | 8/2001 | Smith |
| 6,346,124 B1 | * | 2/2002 | Geiser et al. ................ 600/450 |
| 6,436,048 B1 | | 8/2002 | Pesque |
| 6,447,454 B1 | | 9/2002 | Chenal et al. |

* cited by examiner

*Primary Examiner*—Marvin M. Lateef
*Assistant Examiner*—Maulin Patel
(74) *Attorney, Agent, or Firm*—W. Brinton Yorks, Jr.

(57) ABSTRACT

A semi-invasive ultrasound imaging system for imaging biological tissue includes a transesophageal probe or a transnasal, transesophageal probe connected to a two-dimensional ultrasound transducer array, a transmit beamformer, a receive beamformer, and an image generator. The two-dimensional transducer array is disposed on a distal portion of the probe's elongated body. The transmit beamformer is connected to the transducer array and is constructed to transmit several ultrasound beams over a selected pattern defined by azimuthal and elevation orientations. The receive beamformer is connected to the transducer array and is constructed to acquire ultrasound data from the echoes reflected over a selected tissue volume. The tissue volume is defined by the azimuthal and elevation orientations and a selected scan range. The receive beamformer is constructed to synthesize image data from the acquired ultrasound data. The image generator is constructed to receive the image data and generate images that are displayed on an image display. Preferably, the image generator is constructed to generate, from the image data, several orthographic projection views over the selected tissue volume.

48 Claims, 34 Drawing Sheets

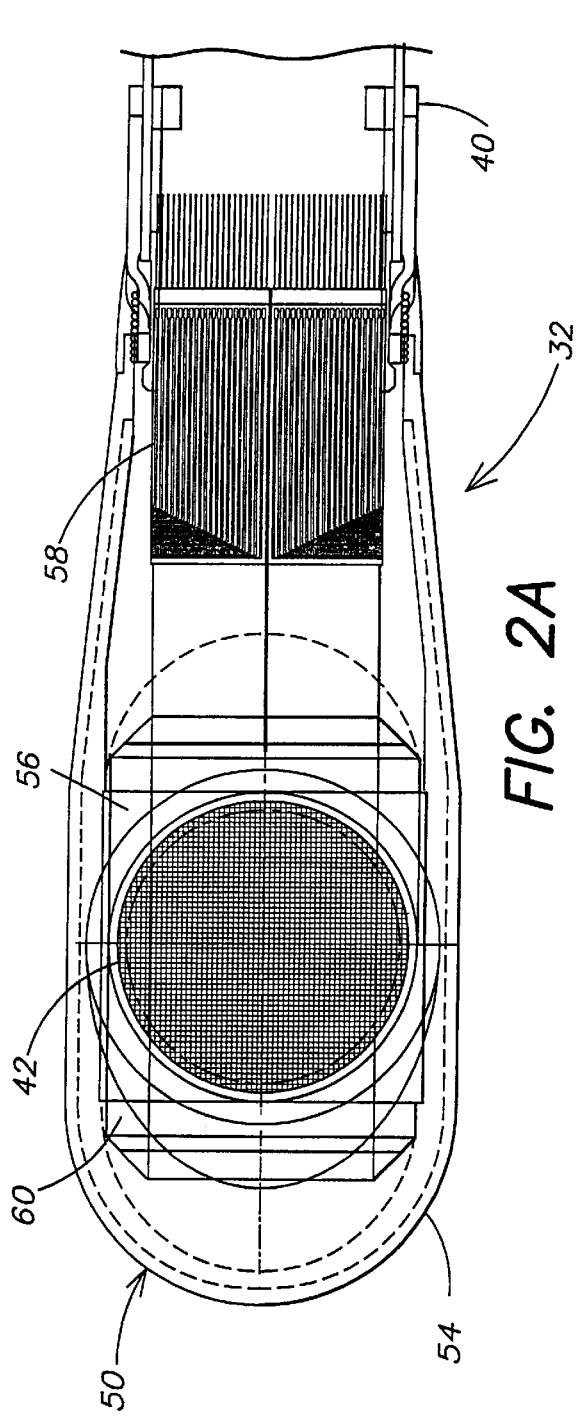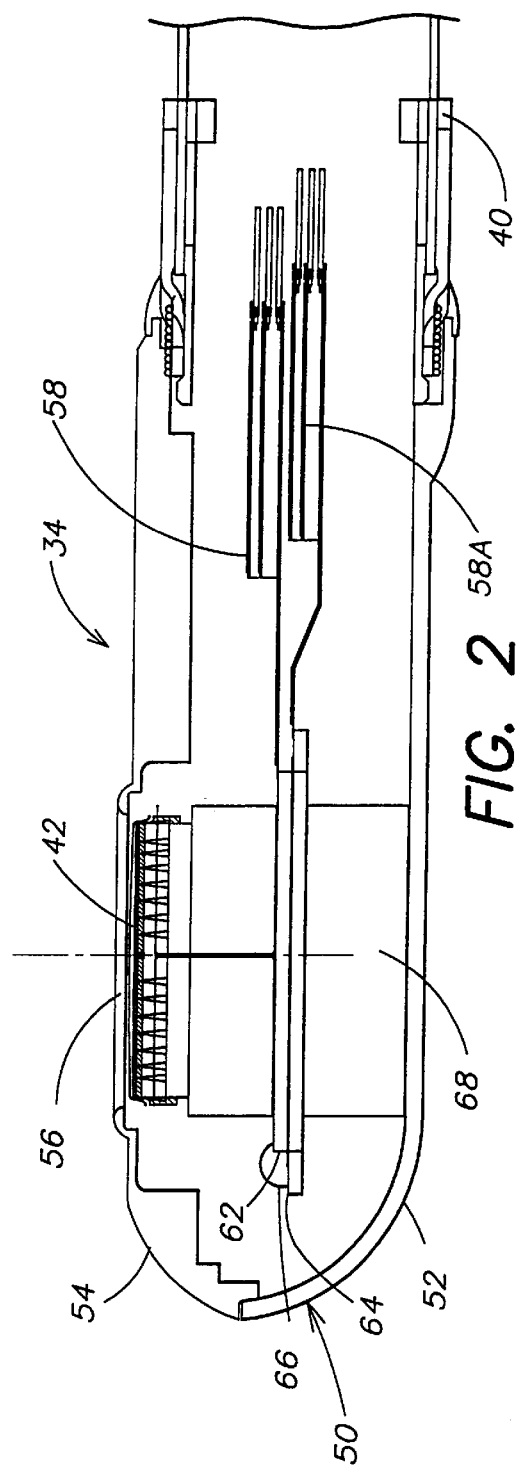

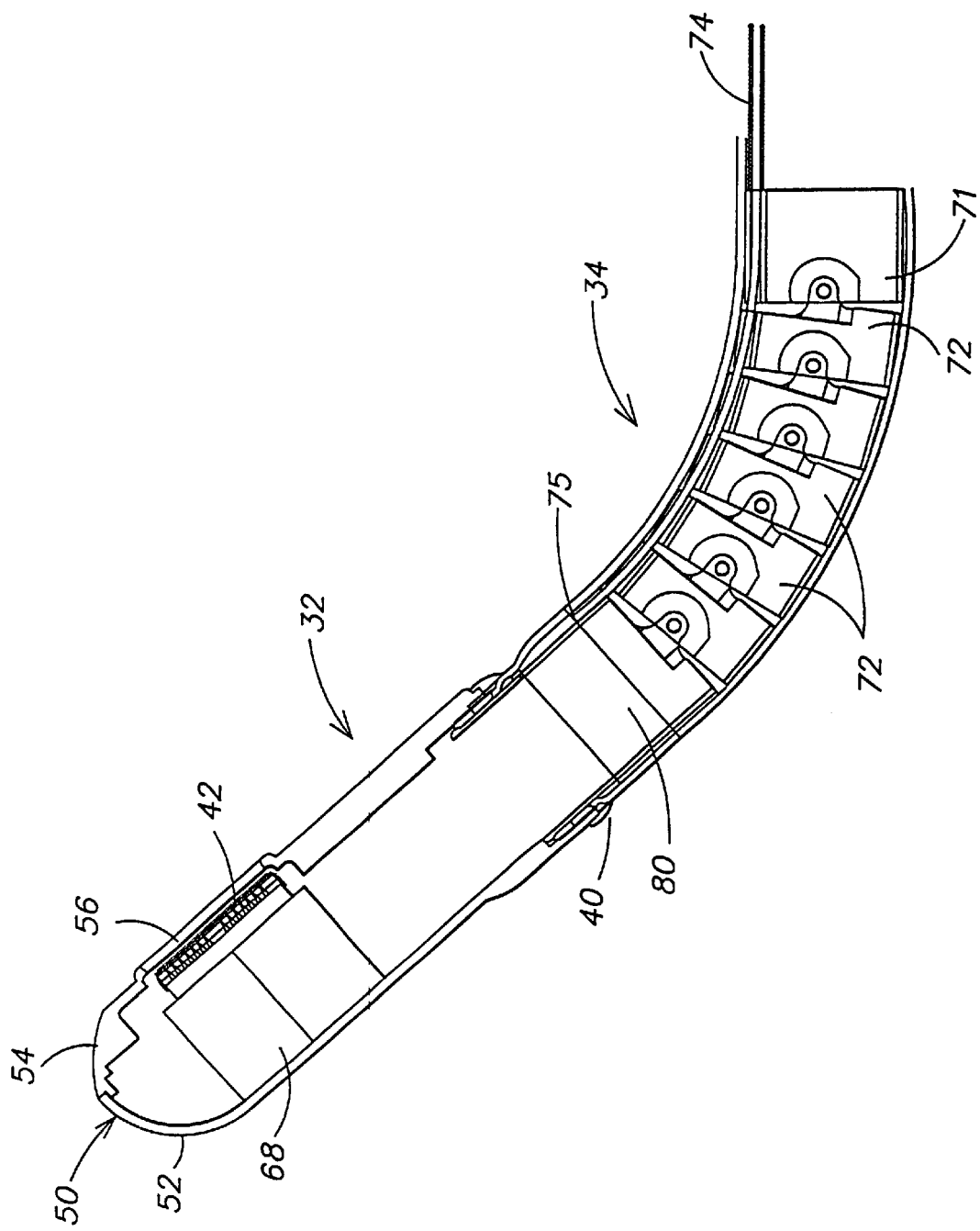

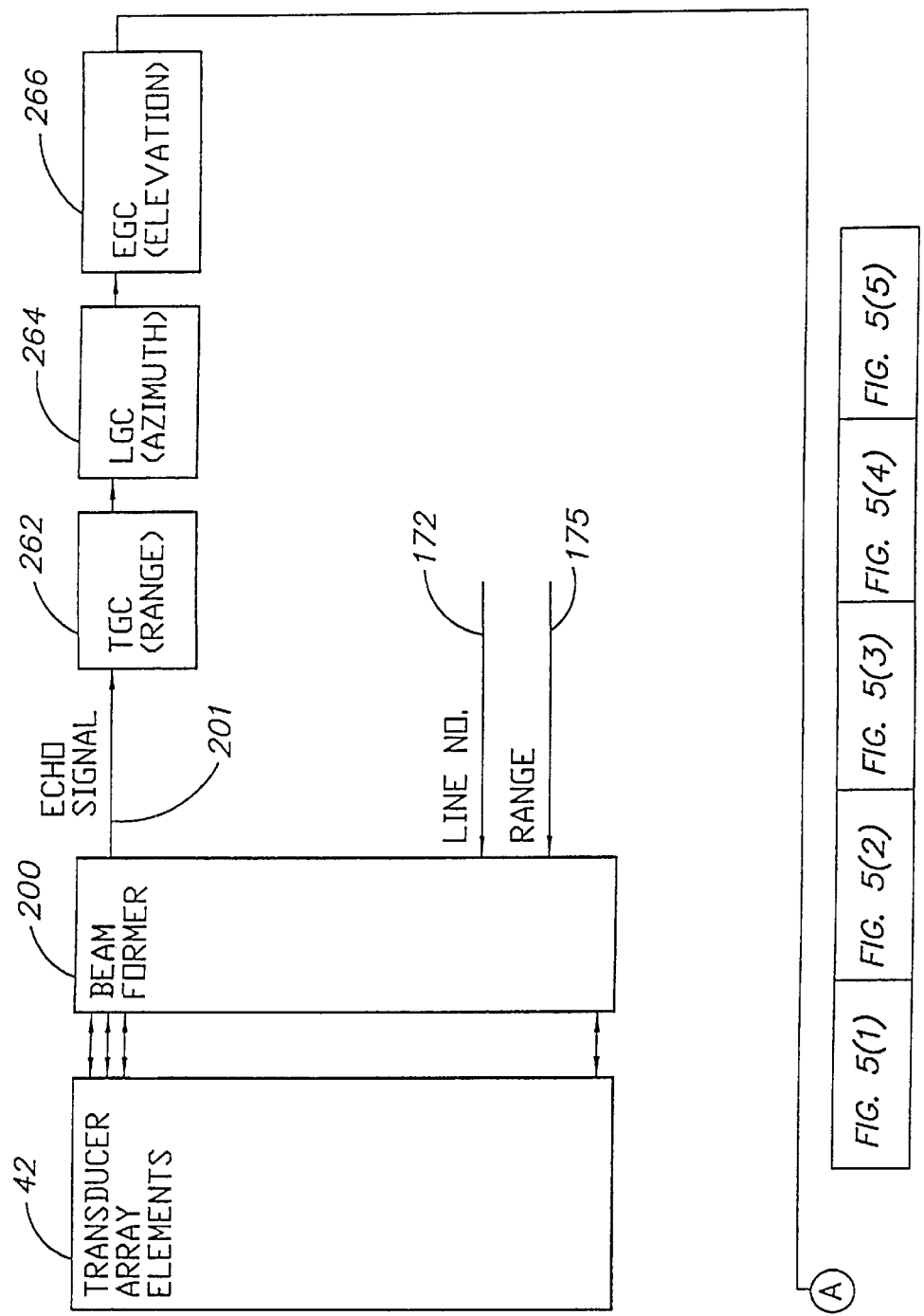

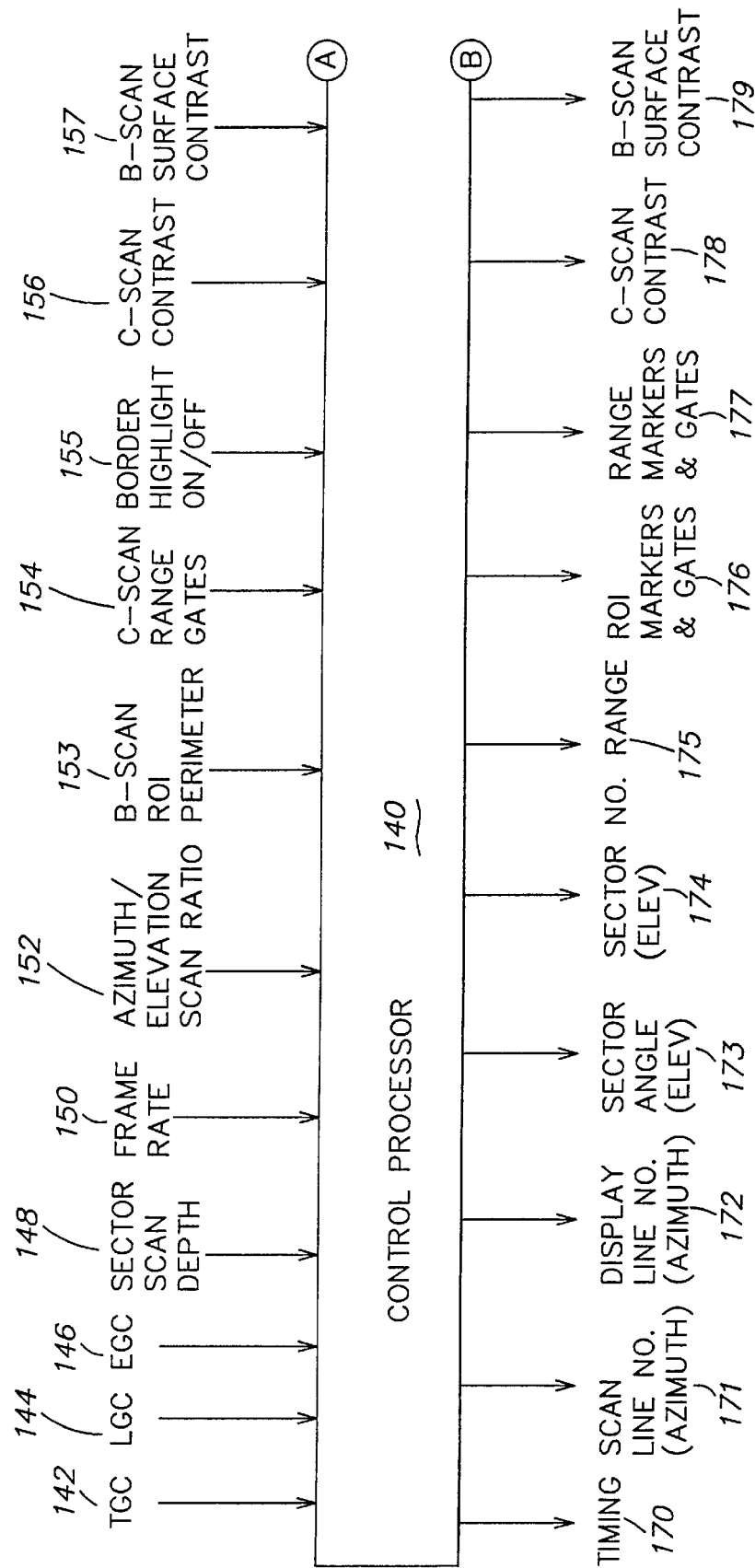
FIG. 5A(1)

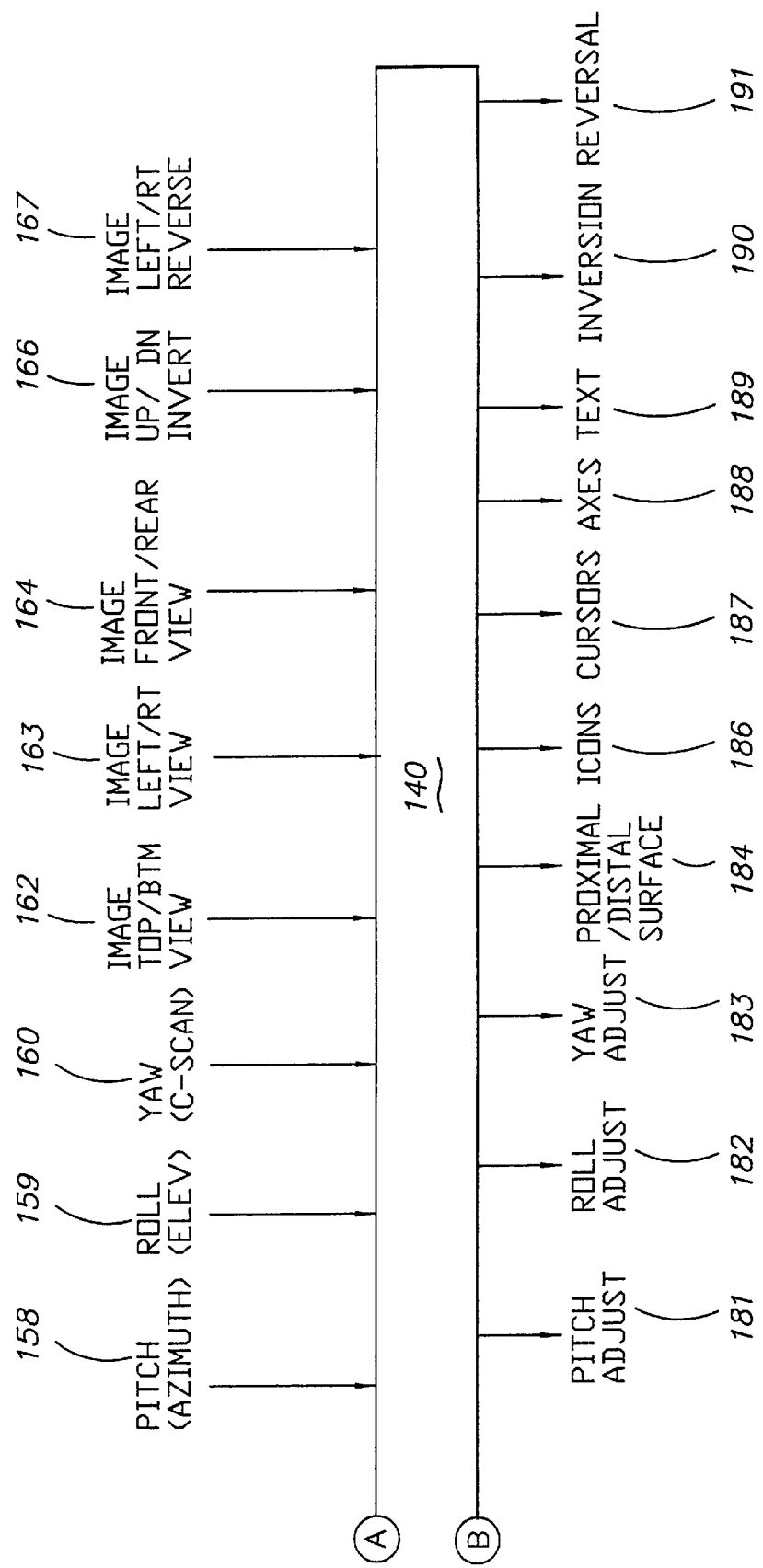
FIG. 5A(2)

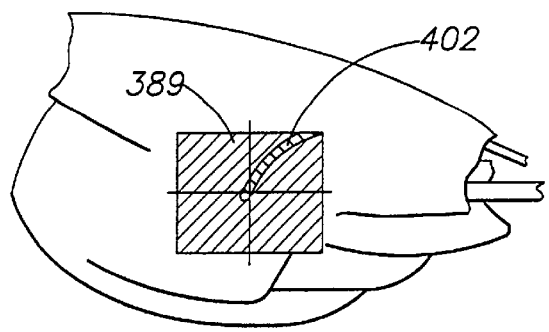
FIG. 9D
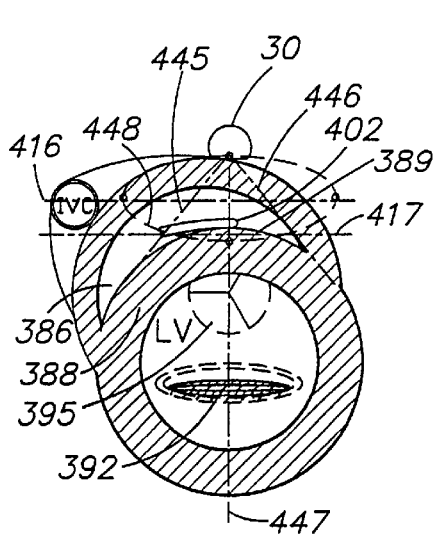
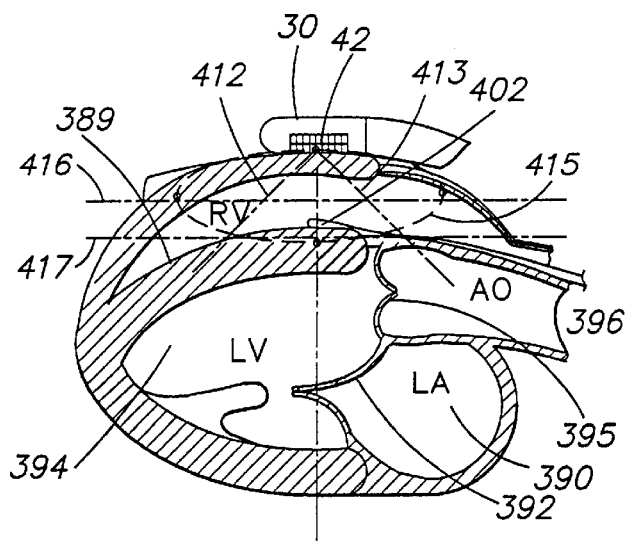
FIG. 9B    FIG. 9A
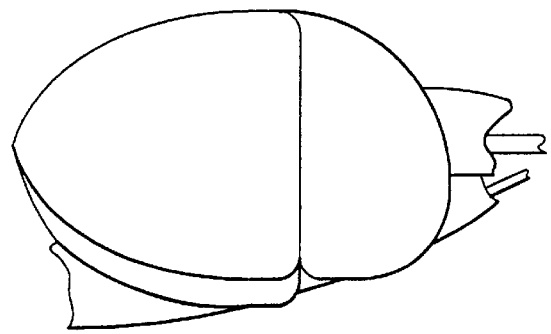
FIG. 9C

TRANSESOPHAGEAL AND TRANSNASAL, TRANSESOPHAGEAL ULTRASOUND IMAGING SYSTEMS

FIELD OF THE INVENTION

The present invention relates to semi-invasive ultrasound imaging systems, and more particularly to transesophageal imaging systems and transnasal, transesophageal imaging systems that provide several two-dimensional plane views and projection views for visualizing three-dimensional anatomical structures inside a patient.

BACKGROUND

Non-invasive, semi-invasive and invasive ultrasound imaging has been widely used to view tissue structures within a human body, such as the heart structures, the abdominal organs, the fetus, and the vascular system. The semi-invasive systems include transesophageal imaging systems, and the invasive systems include intravascular imaging systems. Depending on the type and location of the tissue, different systems provide better access to or improved field of view of internal biological tissue.

In general, ultrasound imaging systems include a transducer array connected to a multiple channel transmit and receive beamformer. The transmit beamformer applies electrical pulses to the individual transducers in a predetermined timing sequence to generate transmit beams that propagate in predetermined directions from the array. As the transmit beams pass through the body, portions of the acoustic energy are reflected back to the transducer array from tissue structures having different acoustic characteristics. The receive transducers (which may be the transmit transducers operating in a receive mode) convert the reflected pressure pulses into corresponding electrical RF signals that are provided to the receive beamformer. Due to different distances from a reflecting point to the individual transducers, the reflected sound waves arrive at the individual transducers at different times, and thus the RF signals have different phases.

The receive beamformer has a plurality of processing channels with compensating delay elements connected to a summer. The receive beamformer selects the delay value for each channel to combine echoes reflected from a selected focal point. Consequently, when delayed signals are summed, a strong signal is produced from signals corresponding to this point. However, signals arriving from different points, corresponding to different times, have random phase relationships and thus destructively interfere. The receive beamformer selects such relative delays that control the orientation of the receive beam with respect to the transducer array. Thus, the receive beamformer can dynamically steer the receive beams to have desired orientations and can focus them at desired depths. The ultrasound system thereby acquires acoustic data.

To view tissue structures in real-time, various ultrasound systems have been used to generate two-dimensional or three-dimensional images. A typical ultrasound imaging system acquires a two-dimensional image plane that is perpendicular to the face of the transducer array applied to a patient's body. To create a three-dimensional image, the ultrasound system must acquire acoustic data over a three-dimensional volume by, for example, moving a one-dimensional (or a one-and-half dimensional) transducer array over several locations. Alternatively, a two-dimensional transducer array can acquire scan data over a multiplicity of image planes. In each case, the system stores the image plane data for reconstruction of three-dimensional images. However, to image a moving organ, such as the heart, it is important to acquire the data quickly and to generate the images as fast as possible. This requires a high frame rate (i.e., the number of images generated per unit time) and fast processing of the image data. However, spatial scanning (for example, when moving a one-dimensional array over several locations) is not instantaneous. Thus, the time dimension is intertwined with the three space dimensions when imaging a moving organ.

Several ultrasound systems have been used to generate 3D images by data acquisition, volume reconstruction, and image visualization. A typical ultrasound system acquires data by scanning a patient's target anatomy with a transducer probe and by receiving multiple frames of data. The system derives position and orientation indicators for each frame relative to a prior frame, a reference frame or a reference position. Then, the system uses the frame data and corresponding indicators for each frame as inputs for the volume reconstruction and image visualization processes. The 3D ultrasound system performs volume reconstruction by defining a reference coordinate system within which each image frame in a sequence of the registered image frames. The reference coordinate system is the coordinate system for a 3D volume encompassing all image planes to be used in generating a 3D image. The first image frame is used to define the reference coordinate system (and thus the 3D volume), uses either three spherical axes ($r_v$, $\Theta_v$ and $\phi_v$ axes) or three orthogonal axes (i.e., $x_v$, $y_v$ and $z_v$ axes). Each image frame is a 2D slice (i.e., a planar image) has two polar axes (i.e., $r_i$ and $\Theta_i$ axes) or two orthogonal axes (i.e., $x_i$ and $y_i$), where i is the i-th image frame. Thus, each sample point within an image plane has image plane coordinates in the image plane coordinate system for such image plane. To register the samples in the reference coordinate system, the sample point coordinates in the appropriate image plane coordinate system are transposed to the reference coordinate system. If an image plane sample does not occur at specific integer coordinates of the reference coordinate system, the system performs interpolation to distribute the image plane sample among the nearest reference coordinate system points.

To store sample data or the interpolated values derived from the sample data, the system allocates memory address space, wherein the memory can be mapped to the reference coordinate system. Thus, values for a given row of a given reference volume slice (taken along, for example, the z-axis) can be stored in sequential address locations. Also, values for adjacent rows in such slice can be stored in adjacent first memory address space. The system performs incremental reconstruction by computing a transformation matrix that embodies six offsets. There are three offsets for computing the x, y, and z coordinates in the x-direction (along the row of the image), and three offsets for computing the x, y, and z coordinates in the y-direction (down the column of the image). Then, the system computes the corners of the reconstruction volume and compares them with the coordinates of the bounding volume. Next, the system determines the intersecting portion of the acquired image and the bounding coordinates and converts them back to the image's coordinate system. This may be done using several digital signal processors.

Furthermore, the system can compute an orthogonal projection of the current state of the reconstruction volume. An orthogonal projection uses simpler computation for rendering (no interpolations need to be computed to transform from the reference coordinate system to a displayed image raster coordinate system). The system can use a maximum intensity projection (MIP) rendering scheme in which a ray is cast along the depth of the volume, and the maximum value encountered is the value that is projected for that ray (e.g., the value used to derive a pixel for a given raster point on the 2D image projection). The system incrementally reconstructs and displays a target volume in real time. The operator can view the target volume and scan effectiveness in real time and improve the displayed images by deliberately scanning desired areas repeatedly. The operator also can recommence volume reconstruction at the new viewing angle.

The image visualization process derives 2D image projections of the 3D volume over time to generate a rotating image or an image at a new viewing angle. The system uses a shear warp factorization process to derive the new 2D projection for a given one or more video frames of the image. For each change in viewing angle, the process factorizes the necessary viewing transformation matrix into a 3D shear which is parallel to slices of the volume data. A projection of the shear forms a 2D intermediate image. A 2D warp can be implemented to produce the final image, (i.e., a 2D projection of the 3D volume at a desired viewing angle). The system uses a sequence of final images at differing viewing angles to create a real-time rotating view of the target volume.

Other systems have been known to utilize power Doppler images alone in a three dimensional display to eliminate the substantial clutter caused by structural information signals. Such Doppler system stores Doppler power display values, with their spatial coordinates, in a sequence of planar images in an image sequence memory. A user can provide processing parameters that include the range of viewing angles. For instance, the user can input a range of viewing angles referenced to a line of view in a plane that is normal to the plane of the first image in the sequence, and a range increment. From these inputs the required number of three dimensional projections is computed. Then, this system forms the necessary sequence of maximum intensity projections by first recalling the planar Doppler power images from the image sequence memory for sequential processing by a scan converter and display processor. The processor rotates each planar image to one of the viewing angles projected back to the viewing plane.

The Doppler system accumulates the pixels of the projected planar images on a maximum intensity basis. Each projected planar image is overlaid over the previously accumulated projected images but in a transposed location in the image plane which is a function of the viewing angle and the interplane spacing: the greater the viewing angle, the greater the transposition displacement from one image to the next. The display pixels chosen from the accumulated images are the maximum intensity pixels taken at each point in the image planes from all of the overlaid pixels accumulated at each point in the image. This effectively presents the maximum intensity of Doppler power seen by the viewer along every viewing line between the viewer and the three dimensional representation.

This system can rotate, project, transpose, overlay, and choose the maximum intensities at each pixel for all of the planar images, and then store in the image sequence memory the resulting three dimensional representation for the viewing angle. The stored three dimensional sequence is available for recall and display upon command of the user. As the sequence is recalled and displayed in real time, the user can see a three dimensional presentation of the motion or fluid flow occurring in the volumetric region over which the planar images were acquired. The volumetric region is viewed three dimensionally as if the user were moving around the region and viewing the motion or flow from changing viewing angles. The viewer can sweep back and forth through the sequence, giving the impression of moving around the volumetric region in two directions.

It has also been known to utilize a modified two dimensional ultrasonic imaging system to provide three dimensional ultrasonic images. Such three dimensional ultrasonic imaging system can use conventional two dimensional ultrasonic imaging hardware and a scan converter. The two dimensional ultrasonic imaging system acquires a plurality of two dimensional images. This system processes the images through scan conversion to approximate their rotation to various image planes and projection back to a reference plane, which can be the original image plane. Conventional scan conversion hardware can be used to rescale the sector angle or depth of sector images, or the aspect ratio of rectangular images. This system projects a plurality of planes for each image and then stores them in a sequence of combined images, wherein each combined image comprises a set of corresponding projected images offset with respect to each other. Each combined image is a different view of a three dimensional region occupied by the planar image information.

The above system can replay the sequence of combined images on a display to depict the three dimensional region as if it is rotating in front of a viewer. Furthermore, the system can recall the stored combined images on the basis of the three dimensional viewing perspectives and displayed sequentially in a three dimensional presentation.

There are several medical procedures where ultrasound imaging systems are not yet widely used. Currently, for example, interventional cardiologists use mainly fluoroscopic imaging for guidance and placement of devices in the vasculature or in the heart. These procedures are usually performed in a cardiac catheterization laboratory (Cathlab) or an electrophysiology laboratory (Eplab). During cardiac catheterization, a fluoroscope uses X-rays on a real-time frame rate to give the physician a transmission view of a chest region, where the heart resides. A bi-plane fluoroscope, which has two transmitter-receiver pairs mounted at 90° to each other, provides real-time transmission images of the cardiac anatomy. These images assist the physician in positioning various catheters by providing him (or her) with a sense of the three-dimensional geometry of the heart.

While fluoroscopy is a useful technique, it does not provide high quality images with good contrast in soft tissues. Furthermore, the physician and the assisting medical staff need to cover themselves with a lead suit and need to reduce the fluoroscopic imaging time whenever possible to lower their exposure to X-rays. In addition, fluoroscopy may not be available for some patients, for example, pregnant women, due to the harmful effects of the X-rays. Recently, transthoracic and transesophageal ultrasound imaging have been very useful in the clinical and surgical environments, but have not been widely used in the Cathlab or Eplab for patients undergoing interventional techniques.

Therefore there is a need for transesophageal or transnasal, transesophageal ultrasound systems and methods that can provide fast and computationally inexpensive real-time imaging. The images should enable effective visualization of the internal anatomy that includes various structures and provide selected views of the tissue of interest. An ultrasound system and method providing anatomically correct and easily understandable, real-time images would find additional applications in medicine.

SUMMARY

The present invention relates to novel transesophageal ultrasound apparatuses or methods for imaging three-dimensional anatomical structures and/or medical devices (e.g., therapy devices, diagnostic devices, corrective devices, stents) introduced inside a patient.

According to one aspect, a transesophageal ultrasound imaging system for imaging biological tissue includes a transesophageal probe connected to a two-dimensional ultrasound transducer array, a transmit beamformer, a receive beamformer, and an image generator. The two-dimensional transducer array is disposed on a distal portion of the probe's elongated body. The transmit beamformer is connected to the transducer array and is constructed to transmit several ultrasound beams over a selected pattern defined by azimuthal and elevation orientations. The receive beamformer is connected to the transducer array and is constructed to acquire ultrasound data from the echoes reflected over a selected tissue volume. The tissue volume is defined by the azimuthal and elevation orientations and a selected scan range. The receive beamformer is constructed to synthesize image data from the acquired ultrasound data. The image generator is constructed to receive the image data and generate images of the selected tissue volume that are displayed on an image display (a video display, a printer, etc.).

Preferred embodiments of this aspect include one or more of the following features:

The image generator is constructed to generate, from the image data, at least two orthographic projection views over the selected tissue volume, and the image display is constructed to display the at least two projection views.

The ultrasound imaging system may include a surface detector and a control processor. The surface detector is constructed to receive image parameters from the control processor and generate surface data from the image data. The image generator is constructed to generate from the surface data a projection image for display on the image display.

The surface detector is a B-scan boundary detector and the image generator is constructed to generate from the image data and the surface data a plane view including the projection image. Furthermore, the image generator may be constructed to generate, from the image data and the surface data, at least two orthographic projection views each including the plane view and the projection image. The surface detector may be a C-scan boundary detector and the image generator is then constructed to generate a C-scan view.

The ultrasound imaging system includes a probe that is a transesophageal probe or a transnasal transesophageal probe. The transesophageal probe includes a locking mechanism co-operatively arranged with an articulation region of the probe and constructed to lock in place the transducer array after orienting the array relative to a tissue region of interest. The transnasal transesophageal probe includes a locking mechanism co-operatively arranged with an articulation region of the probe and constructed to lock in place the transducer array after orienting the array relative to a tissue region of interest.

The transducer array and the beamformers are constructed to operate in a phased array mode and acquire the ultrasound data over the selected azimuthal range for several image sectors each having a designated elevation location. The transducer array includes a plurality of sub-arrays connected to the transmit and receive beamformers.

The image generator is constructed to generate, from the image data, at least two orthographic projection views over the selected tissue volume, and the image display is constructed to display the at least two projection views. The image generator is constructed to generate two of the orthographic projection views as orthogonal B-scan views and generate one of the orthographic projection views as a C-scan view.

The transesophageal probe may also include a locking mechanism co-operatively arranged with an articulation region of the probe and constructed to lock in place the transducer array after orienting the array relative to a tissue region of interest.

The ultrasound imaging system includes a control processor constructed and arranged to control the transmission of the ultrasound beams and control the synthesis of the image data based on range data provided by a user. The transducer array includes a plurality of sub-arrays connectable to the transmit and receive beamformers and the control processor is constructed to control arrangement of the sub-arrays for optimizing acquisition of the echo data of the tissue volume. The control processor constructed and arranged to provide to the transmit beamformer and the receive beamformer scan parameters that include an imaging depth, a frame rate, or an azimuth to elevation scan ratio.

The control processor is constructed to receive input data and provide output data causing the transmit and receive beamformers to change the azimuthal range. The control processor is constructed to receive input data and provide output data causing the transmit and receive beamformers to change the elevation range. The control processor is constructed to provide data to image generator for adjusting a yaw of the views by recalculating the orthographic projection views. By changing the azimuthal range or the elevation range, a clinician can direct the scan over a smaller data volume centered on the tissue of interest. By scanning over the smaller volume, the system improves real-time imaging of moving tissue by increasing the frame rate, because it collects a smaller number of data points.

The image generator includes at least one view interpolation processor constructed to generate the at least two orthographic projection views, at least one icon generator constructed to generate the at least two icons associated with the at least two orthographic projection views, and includes at least one boundary detector constructed and arranged to detect a tissue boundary.

The view interpolation processor is arranged to generate a B-scan view and a C-scan view, the C-scan view is generated by receiving C-scan designation information from the B-scan view. The view interpolation processor is an azimuthal view interpolation processor. The view interpolation processor is an elevation view interpolation processor. The view interpolation processor includes a gated peak detector.

The boundary detector is a B-scan boundary detector and the interpolation processor is further arranged to receive from the B-scan boundary detector data for highlighting borders in the orthographic projection views. The boundary detector is a C-scan boundary detector and the interpolation processor is further arranged to receive from the C-scan boundary detector data for highlighting borders in the orthographic projection views.

The image generator includes a yaw adjustment processor. The image generator includes a range processor constructed to provide two range cursors for generating a C-scan projection view. The range processor is arranged to receive a user input defining the two range cursors. The icon generator constructed to generate an azimuthal icon displaying the azimuthal angular range and displaying a maximum azimuthal angular range. The icon generator constructed to generate an elevation icon displaying the elevation angular range and displaying a maximum elevation angular range.

According to another aspect, a transesophageal ultrasound imaging method is performed by introducing into the esophagus a transesophageal probe and positioning a two-dimensional ultrasound transducer array at a selected orientation relative to an tissue region of interest, transmitting ultrasound beams over a plurality of transmit scan lines from the transducer array over a selected azimuthal range and a selected elevation range of locations, and acquiring by the transducer array ultrasound data from echoes reflected from a selected tissue volume delineated by the azimuthal range, the elevation range and a selected sector scan depth and synthesizing image data from the acquired ultrasound data. Next, the ultrasound imaging method is performed by generating images from the image data of the selected tissue volume, and displaying the generated images.

Preferably, the transesophageal ultrasound imaging method may be performed by one or more of the following: The transmitting and the acquiring is performed by transmit and receive beamformers constructed to operate in a phased array mode and acquire the ultrasound data over the selected azimuthal range for several image sectors having known elevation locations. The generating includes generating at least two orthographic projection views over the tissue volume, and the displaying includes displaying at least two orthographic projection views.

The imaging method may be used for positioning a surgical instrument at a tissue of interest displayed by the orthographic projection views. The imaging method may be used for verifying a location of the surgical instrument during surgery based orthographic projection views. The imaging method may be used for performing the transmitting, the acquiring, the generating, and the displaying of the orthographic projection views while performing surgery with the surgical instrument. The imaging method may be used for performing the transmitting, the acquiring, the generating, and the displaying of the orthographic projection views after performing surgery with the surgical instrument.

The generation of at least two orthographic projection views may include generating a selected C-scan view. The generation of the selected C-scan view may include providing a C-scan designation for the selected C-scan view. The designation may include defining a bottom view or defining a top view. The generation of the C-scan may include detecting a tissue boundary by using a C-scan boundary detector, and selecting ultrasound data for the C-scan by a gated peak detector.

The imaging method may include providing input data to a control processor and providing output data from the control processor to direct the transmit and receive beamformers to change the azimuthal range. The imaging method may include providing input data to a control processor and providing output data from the control processor to direct the transmit and receive beamformers to change the elevation range. The control processor may also provide data to image generator for adjusting a yaw of the views by recalculating the orthographic projection views. By changing the azimuthal range or the elevation range, a clinician can direct the scan over a smaller data volume centered on the tissue of interest. By scanning over the smaller volume, the system improves real-time imaging of moving tissue by increasing the frame rate, because it collects a smaller number of data points.

The generation of at least two orthographic projection views may include generating an azimuthal icon associated with the selected azimuthal range and a maximum azimuthal range, or an elevation icon associated with the selected elevation range and a maximum elevation range.

BRIEF DESCRIPTION OF THE DRAWINGS

FIGS. 2 and 2A are schematic cross-sectional views of a rigid region of the transesophageal imaging probe.

FIG. 3 shows a schematic cross-sectional view of an articulation region of the transesophageal probe articulated as an in-plane J hook.

FIGS. 5A(1)–5A(2) shows diagrammatically a control processor of the ultrasound system of FIG. 1.

FIGS. 9A and 9B are cross-sectional views of the human heart with the imaging probe inserted in the esophagus and an ablation catheter positioned in the right ventricle.

FIG. 9C is a projection view of the human heart.

FIG. 9D is a projection view of the human heart including a cut-away top view displaying the ablation catheter.

DETAILED DESCRIPTION OF THE PREFERRED EMBODIMENTS

Figure 1:
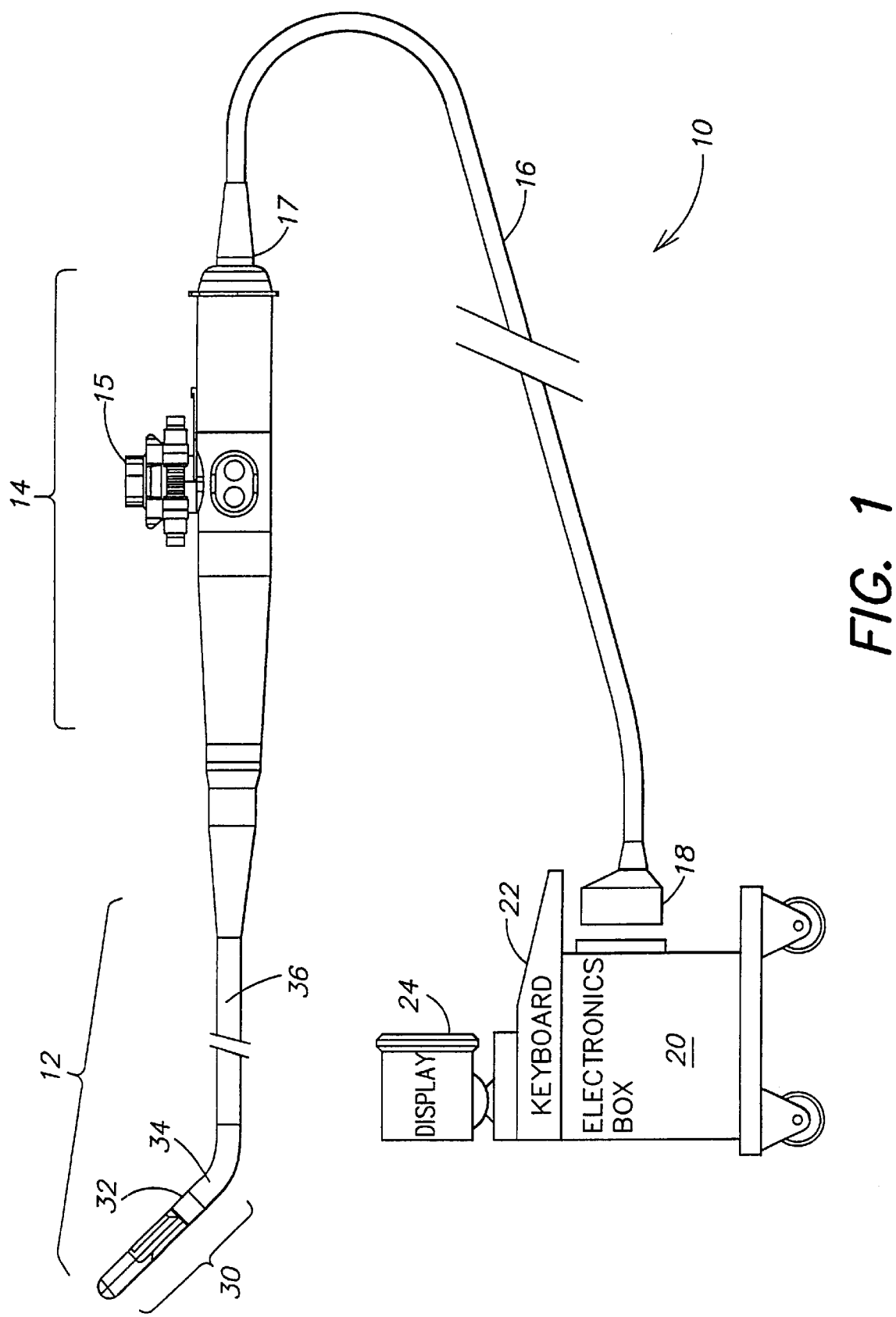
FIG. 1 illustrates an ultrasound system including a transesophageal imaging probe having a distal part and a semi-flexible elongated body.

Referring to FIG. 1, a transesophageal (TEE) imaging system 10 includes a transesophageal probe 12 with a probe handle 14, connected by a cable 16, a strain relief 17, and a connector 18 to an electronics box 20. Electronics box 20 is interfaced with a keyboard 22 and provides imaging signals to a video display 24. Electronics box 20 includes a transmit beamformer, a receive beamformer, and an image generator. Transesophageal probe 12 has a distal part 30 connected to an elongated semi-flexible body 36. The proximal end of elongated part 36 is connected to the distal end of probe handle 14. Distal part 30 of probe 12 includes a rigid region 32 and a flexible region 34, which is connected to the distal end of elongated body 36. Probe handle 14 includes a positioning control 15 for articulating flexible region 34 and thus orienting rigid region 32 relative to tissue of interest. Elongated semi-flexible body 36 is constructed and arranged for insertion into the esophagus. Transesophageal probe 12 can be made by using a commercially available gastroscope and the distal rigid region shown in FIGS. 2 and 2A. The entire insertion tube is about 110 cm long and has about 30F in diameter. The gastroscope is made, for example, by Welch Allyn (Skananteles Falls, N.Y.).

Referring to FIGS. 2 and 2A, the transesophageal imaging probe 12 includes distal rigid region 32 coupled to flexible region 34 at a coupling region 40. Distal region 32 includes a distal tip housing 50 for encasing an ultrasound transducer array 42, electrical connections and associated electronic elements. Transducer array 42 is preferably a two-dimensional array of ultrasound transducer elements. Distal tip housing 50 includes a lower tip housing 52 and an upper tip housing 54 having a ultrasonic window 56 and a matching medium located in front of transducer array 42. The front part of tip housing 50 has a bullet shape with a rounded tip (or pill shape) for easy introduction into the fornix and advancement in the esophagus. Furthermore, housing 54 has a convex shape around window 56. Ultrasonic window 56 may also include an ultrasonic lens and a metal foil embedded in the lens material for cooling purposes.

Transducer array 42 is bonded to an array backing 60 and the individual transducer elements are connected to an integrated circuit 62, as described in U.S. Pat. No. 5,267, 221. Integrated circuit 62 is connected to a circuit board 64 using wire bonds 66. This structure is thermally connected to a heat sink 68. The transesophageal probe includes two super flex circuits 58 and 58A, which provide connections between circuit board 64 and probe connector 18. The super flex circuits are arranged to have isotropic bending properties, for example, by folding into an accordion shape or by wrapping into a spiral shape. Alternatively, the super flex circuits may be replaced by a coaxial cable.

Alternatively, imaging system 10 may use a transnasal, transesophageal imaging probe. The transnasal, transesophageal imaging probe includes an insertion tube connected to a distal part with a two-dimensional transducer array. The insertion tube is about 100 cm to 110 cm long and has a diameter of about 10F to 20F. The two-dimensional transducer array is bonded to an array backing and the individual transducer elements are connected to an integrated circuit, as described in detail above.

Figure 3A:
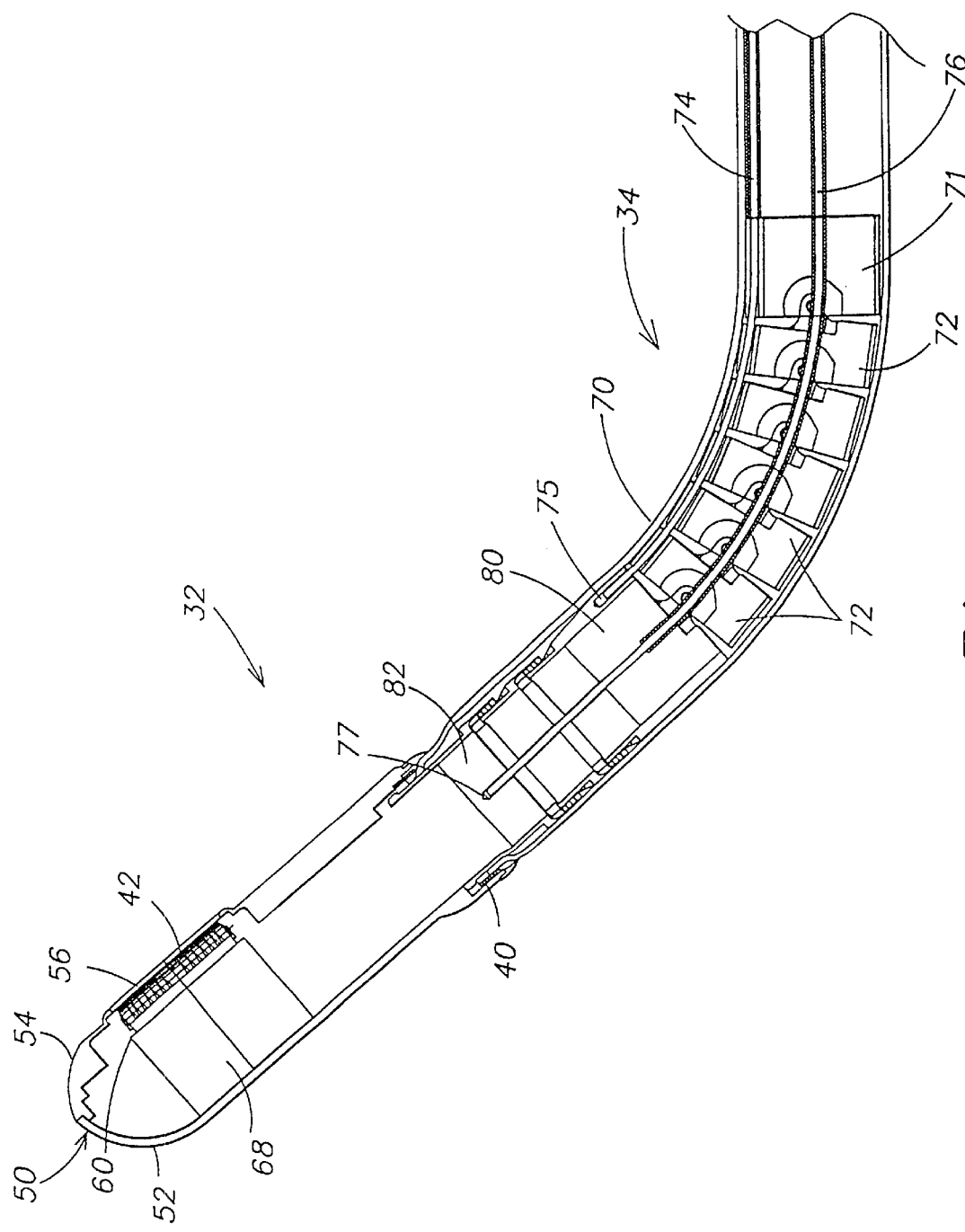
FIG. 3A shows a schematic cross-sectional view of the articulation region of the transesophageal probe articulated as an out-of-plane J hook.
Figure 3B:
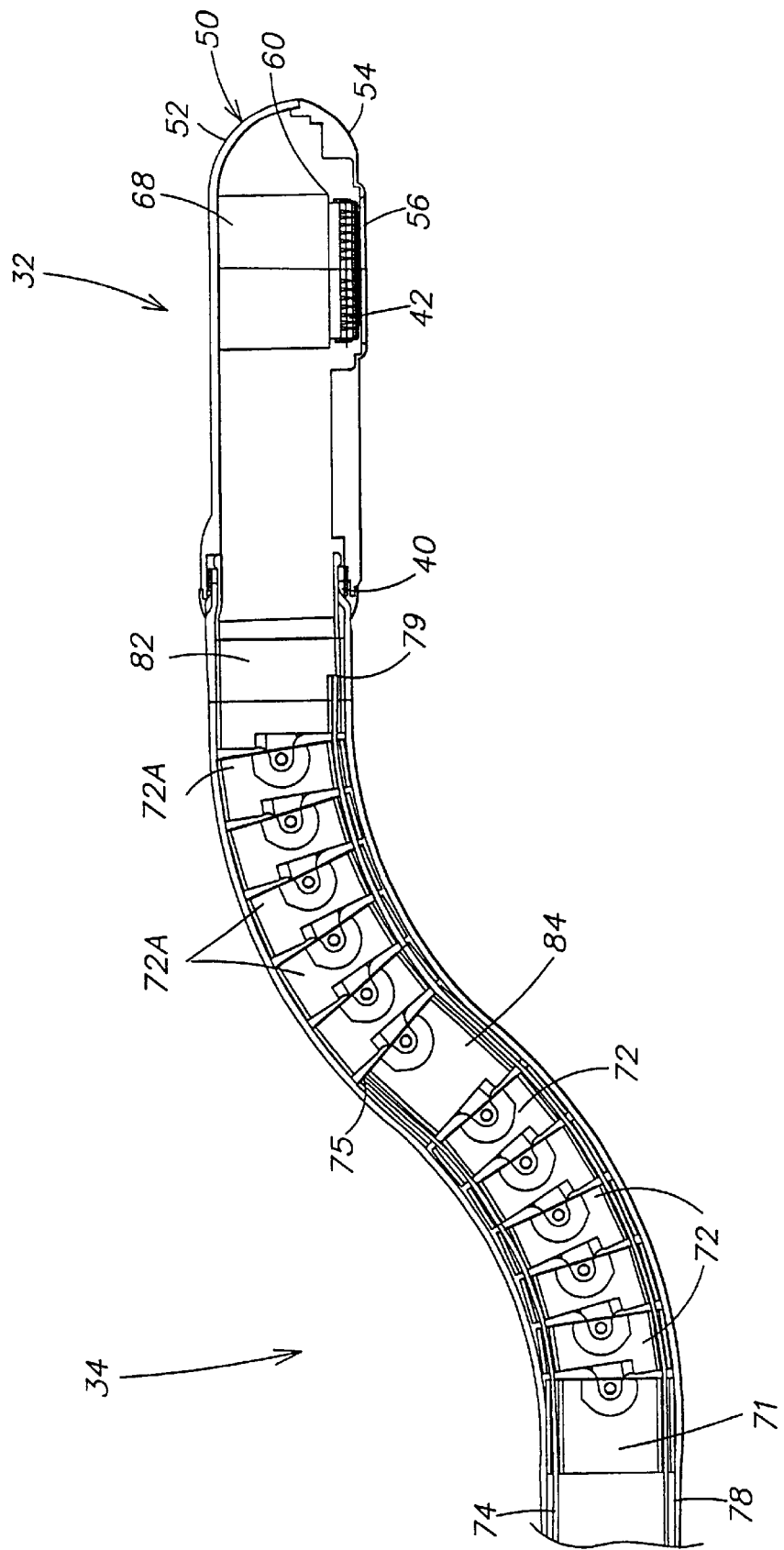
FIG. 3B shows a schematic cross-sectional view of the articulation region of the transesophageal probe articulated as an in-plane S hook.
Figure 8:
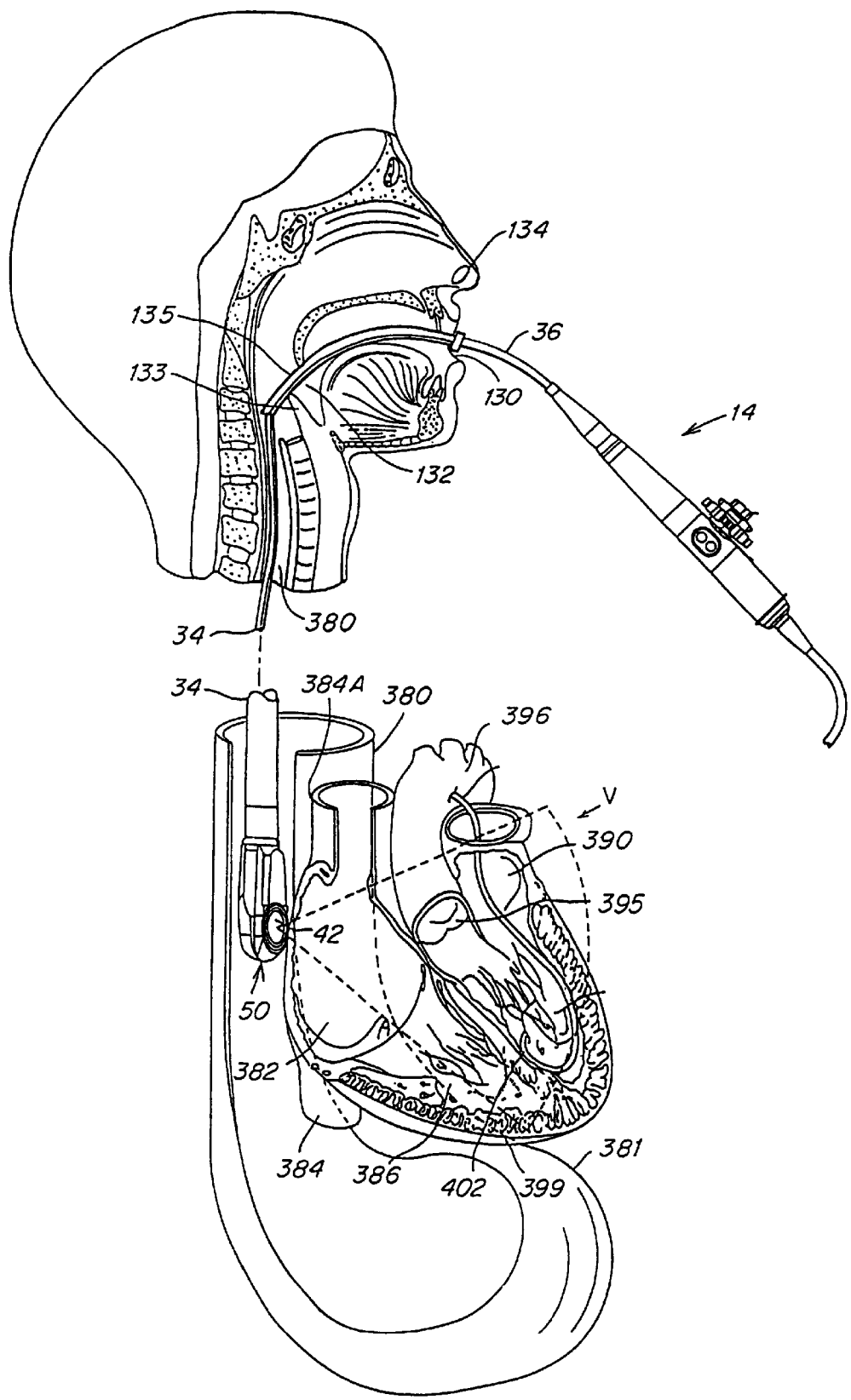
FIGS. 8, 8A, 8B and 8C illustrate introduction and use of the transesophageal probe and the transnasal transesophageal probe for imaging of the heart.
Figure 8A:
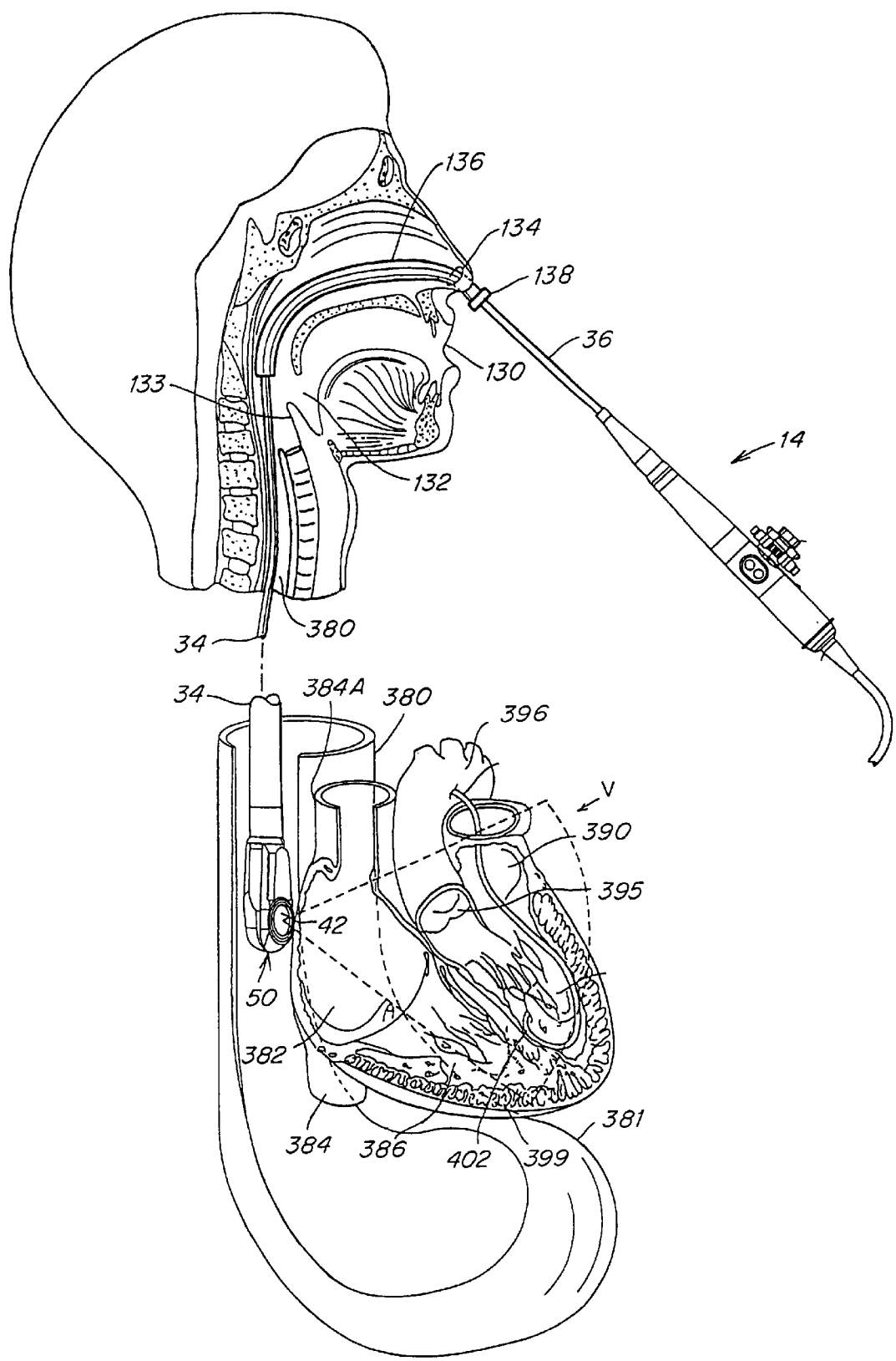

FIGS. 3, 3A and 3B are schematic cross-sectional views of flexible region 34 of transesophageal imaging probe 12. Imaging probe 12 includes an articulation mechanism coupled to positioning control 15 (FIG. 1) for articulating flexible region 34. Flexible region 34 exhibits torsional stiffness and substantially no torsional play. As described below, a clinician adjusts positioning control 15 (FIG. 1) to articulate in various ways flexible region 34 in order to position rigid distal region 32 and orient transducer array 42 relative to a tissue volume of interest (as shown in FIGS. 8 and 8A). The clinician then can lock the articulated flexible region 34 in place to maintain the position of transducer array 42 during the probe manipulation or ultrasonic examination. In a preferred embodiment, flexible region 34 includes a plurality of articulation links 71, 72 or 80 cooperatively arranged with at least one push-pull cable (or rod) controllable by positioning control knobs 15. The articulation links are covered by a flexible sheath 70.

Figure 3C:
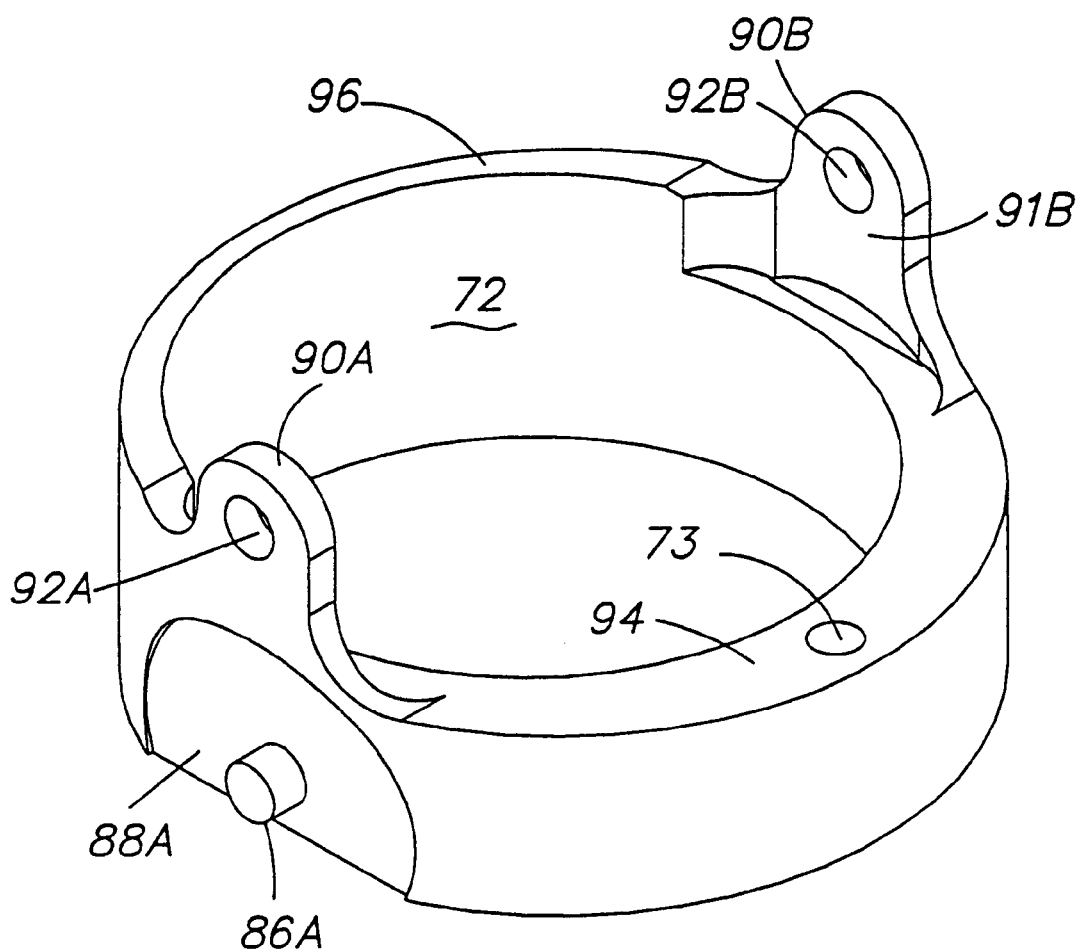
FIG. 3C is a perspective view of an articulation link used in the articulation region of the transesophageal probe.

FIG. 3 shows flexible region 34 articulated as an in-plane J hook. Flexible region 34 is made of a proximal link 71, a set of links 72 (shown in detail in FIG. 3C), and a distal link 80 connected to the distal end of highly flexible pull-push rod 74 at a connection 75. Positioning control knobs 15 control one or several rack and pinion mechanisms located in handle 14. When the rack and pinion mechanism proximally displaces push-pull rod 74, flexible region 34 bends and forms the in-plane J hook, wherein rigid distal region 32 and flexible region 34 are within the same plane. This in-plane bend is facilitated by the design of articulation link 72 cooperatively arranged with push-pull rod 74 connected to distal link 80 at its distal end. Articulation link 72 is shown in FIG. 3C.

Referring to FIG. 3C, articulation link 72 has a ring-like structure that includes a pivotable hinge connecting two neighboring links 72. The pivotable hinge includes two hinge pins 86A and 86B (not visible in this perspective view) disposed on the opposite sides of link 72 and extending from recessed surfaces 88A and 88B (again not visible), respectively. Hinge lips 90A and 90B include inside surfaces 91A (again not shown but described to illustrate the symmetry) and 91B, which have a complementary shape to the shape of surfaces 88A and 88B. Hinge lips 90A and 90B also include holes 92A and 92B, respectively, which are shaped to receive the hinge pins.

Articulation link 72 also includes a stop surface 94 and a stop surface 96. Stop surface 94 is positioned to provide a pre-selected maximum bending of articulation region 34, facilitated by each link, upon the pulling action of push-pull rod 74. Stop surface 96 is positioned at a height that enables articulation region 34 to assume a straight orientation when push-pull rod 74 disposed in channel 73 does not pull on distal link 80. Alternatively, stop surface 96 is designed for articulation region 34 to assume any selected orientation. For example, stop surface 96 may be designed for articulation region 34 to assume an opposite bend when push-pull rod 74 pushes on distal link 80. Articulation links 72 are made of a plastic or metal, such as brass or stainless steel that can also provide electrical shielding for electrical wires located inside. The surface of articulation links 72 is designed to carry sheath 70 while articulation links 72 can still bend readily without gripping or pinching sheath 70.

FIG. 3A shows distal part 30 articulated as an out-of-plane J hook. Flexible region 34 includes proximal link 71, distal link 80 and another set of distal links 82. Push-pull rod 74 extends in channel 73 (FIG. 3C) from a rack and pinion mechanism to a connection 75 in link 80. Push-pull rod 76 extends from a distal end 77 connected to distal link 82 to another rack and pinion mechanism (not shown) near handle 14. Push-pull rod 74 is displaced proximally to bend articulation region 34. Push-pull rod 76 displaces distal link 82, connected to rigid distal region 32; these two displacements form the out-of-plane J hook having flexible region 34 displaced out of the plane of rigid distal region 32.

FIG. 3B shows distal part 30 articulated as an in-plane S hook. Flexible region 34 includes proximal link 71, sets of links 72A, an anchoring link 84, a set of links 72, and distal link 82 connected to distal rigid region 32. Push-pull rod 74 extends from its distal end 75, connected to link 84, to a rack and pinion mechanism located near handle 14. Push-pull rod 78 extends from its distal end 79, connected to link 82, through links 72, link 84, links 72A and link 71 to another rack and pinion mechanism located in the catheter handle. Articulation links 72A are basically mirror images of links 72, but include two channels for accommodating push-pull rods 74 and 78. Links 72 enable articulation in one orientation, and links 72A enable articulation in a 180 degree symmetric orientation. By proximally displacing push-pull rod 74, the rack and pinion mechanism actuates displacement of the proximal part of articulation region 34 in one direction. Furthermore, by proximally displacing push-pull rod 78, the rack and pinion mechanism bends the distal part of articulation region 34 in another direction, thereby forming the in-plane S hook. That is, the in-plane S hook has flexible region 34 and distal rigid region 32 located in the same plane.

The articulation region shown in FIG. 3B may be further modified to include push-pull rod 76 placed inside modified link 72 as shown in link 72A. By proximally displacing push-pull rod 76, articulation region 34 forms an out-of-plane S hook. The out-of-plane S hook has flexible region 34 located in one plane and distal rigid region 32 bend out of that plane. This arrangement enables both tilting transducer array 42 and pulling it back to achieve a desired distance from the tissue of interest. A clinician manipulates the control knobs 15 until the tip of the probe has been articulated to a position where transducer array 42 has a desired orientation relative to the tissue volume of interest. When transducer array 42 is properly positioned the physician locks the articulation mechanism in its current position using a brake. After the articulation mechanism is locked, the imaging system collects the echo data, as shown in FIGS. 8 and 8A.

Figure 4:
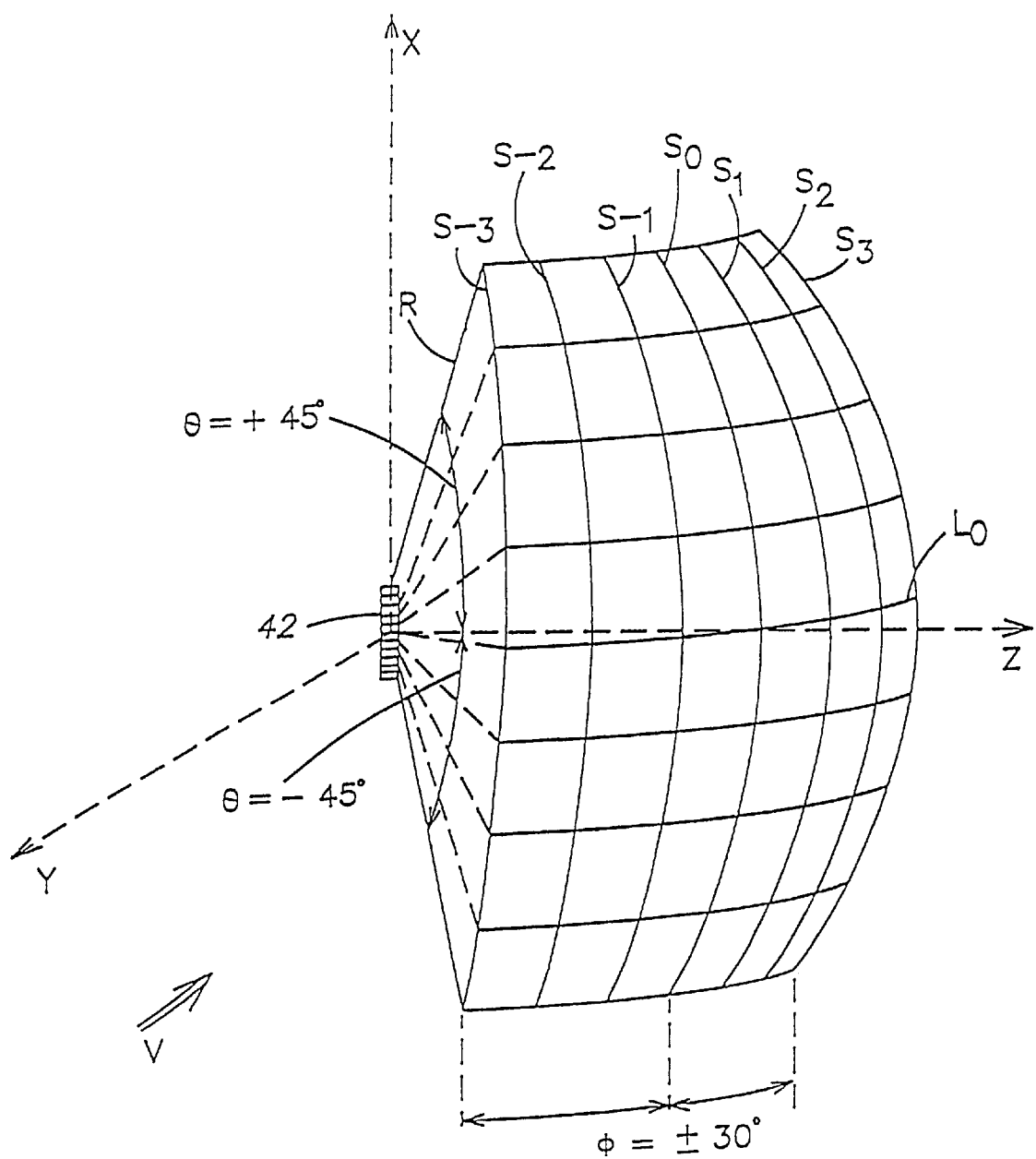
FIG. 4 shows a scanned volume of echo data used for illustration of orthographic projection views.
Figure 5:
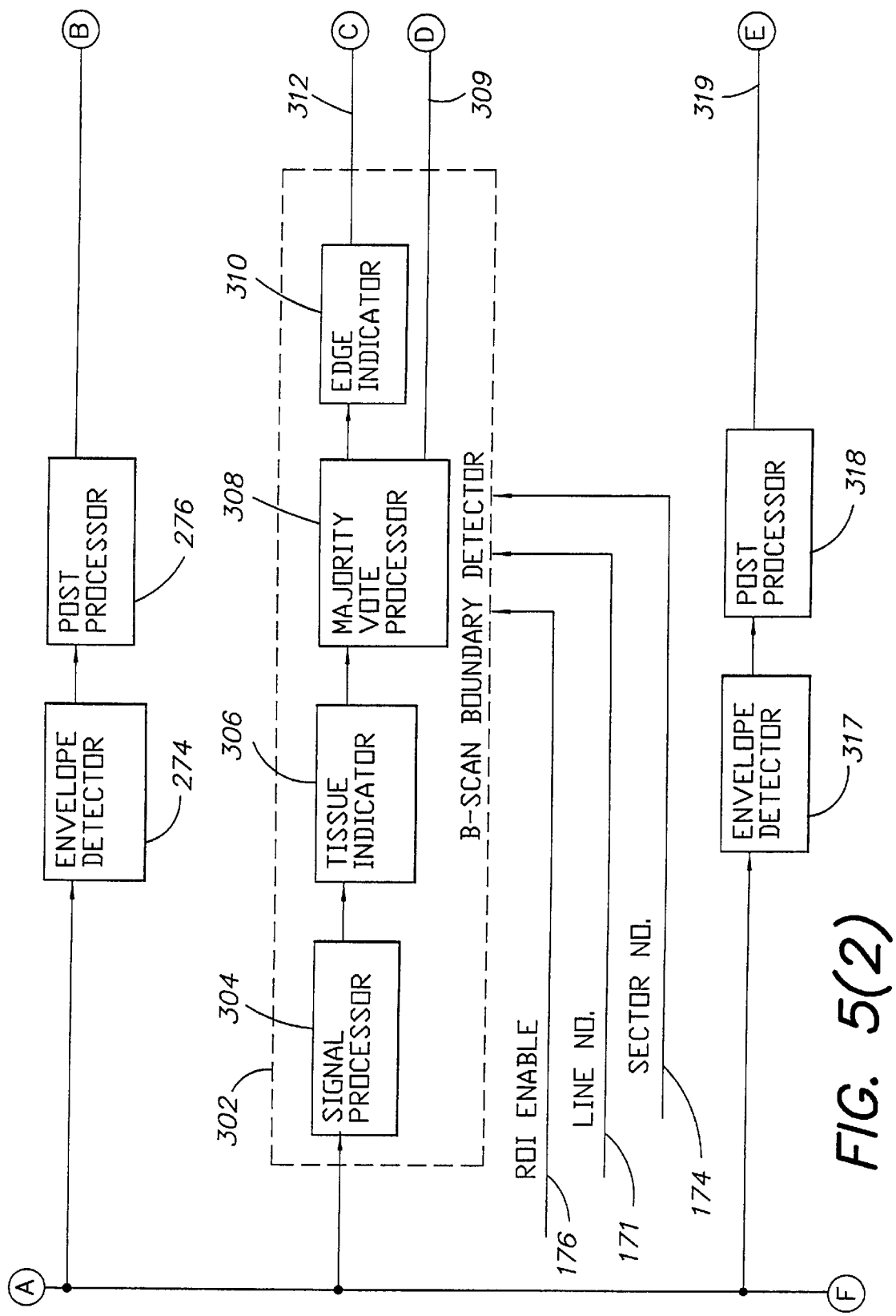
FIGS. 5(1)–5(5) shows diagrammatically an image generator of the ultrasound system of FIG. 1.
Figure 5:
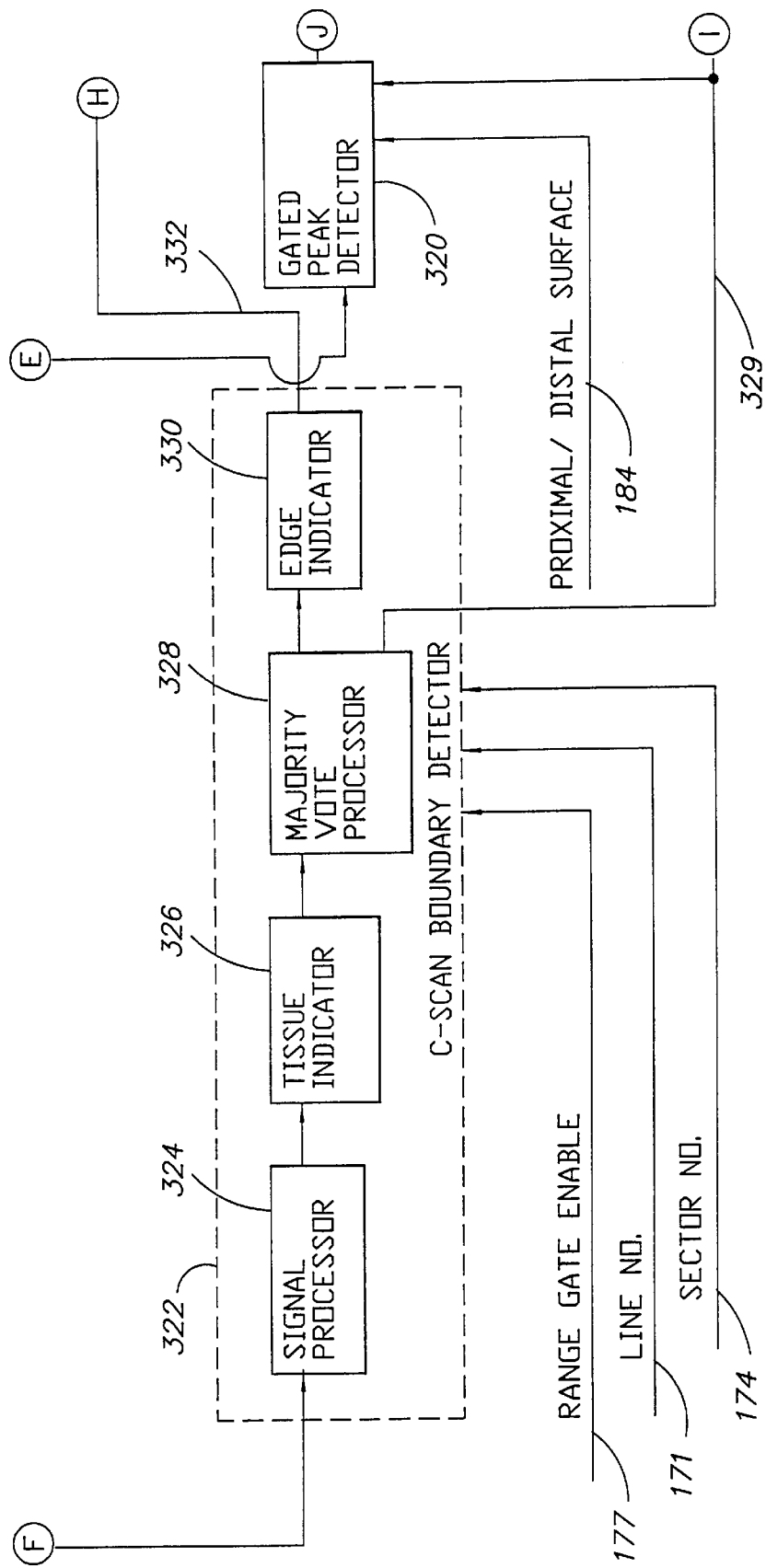
Figure 5:
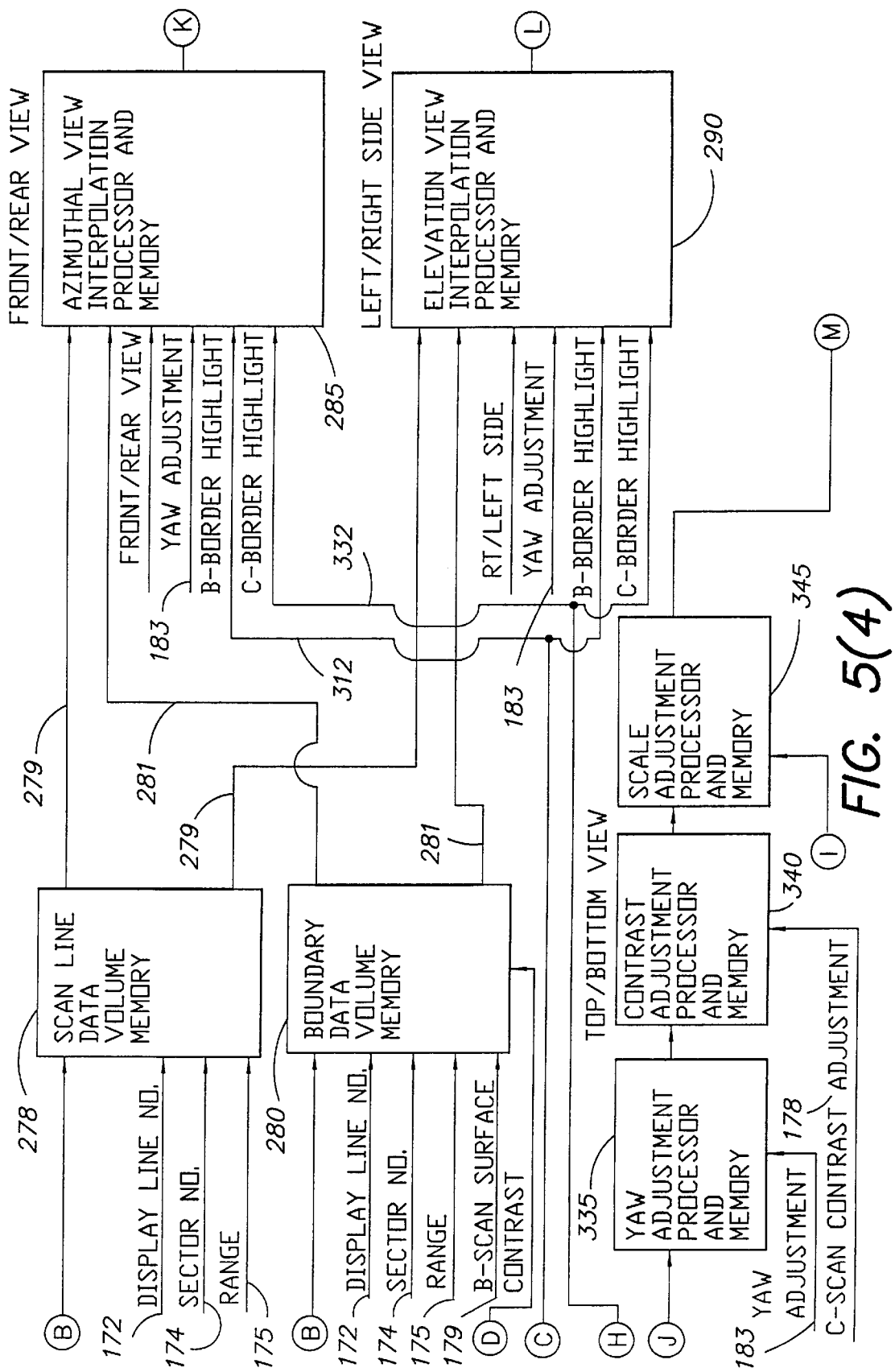
Figure 5:
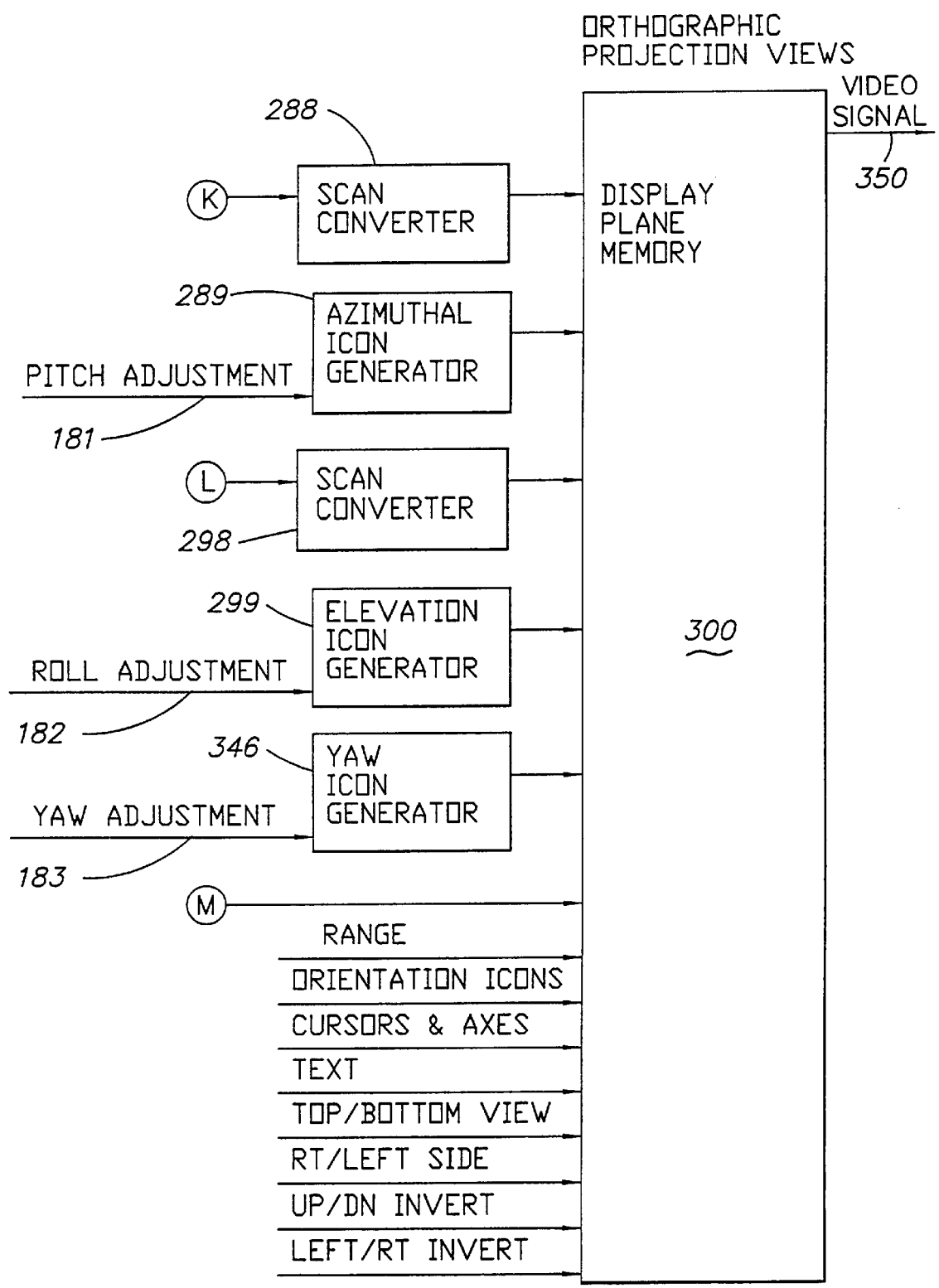
Figure 5B:
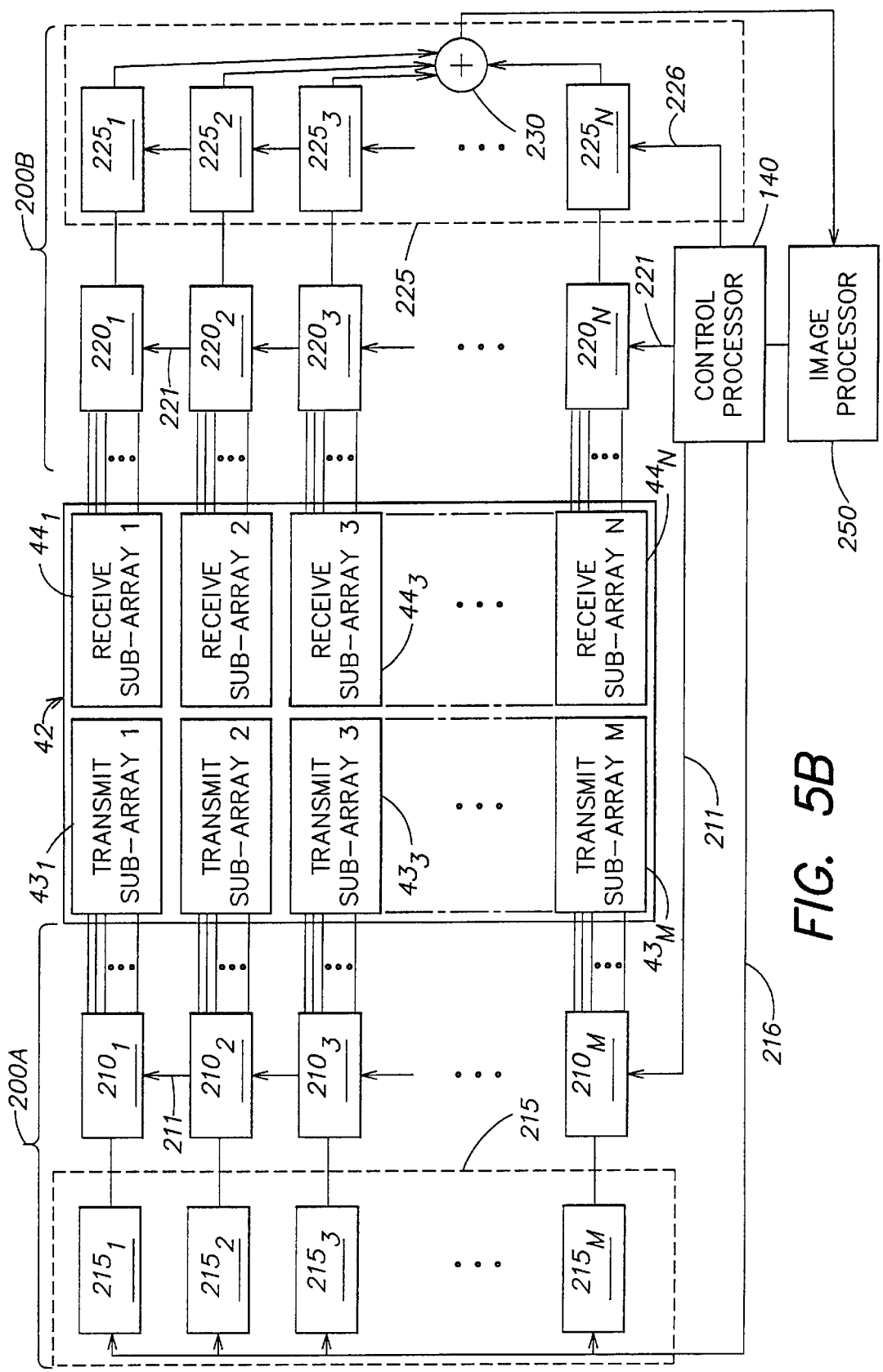
FIG. 5B shows diagrammatically an array of ultrasound transducers connected to a transmit beamformer and a receive beamformer of the ultrasound system.
Figure 5C:
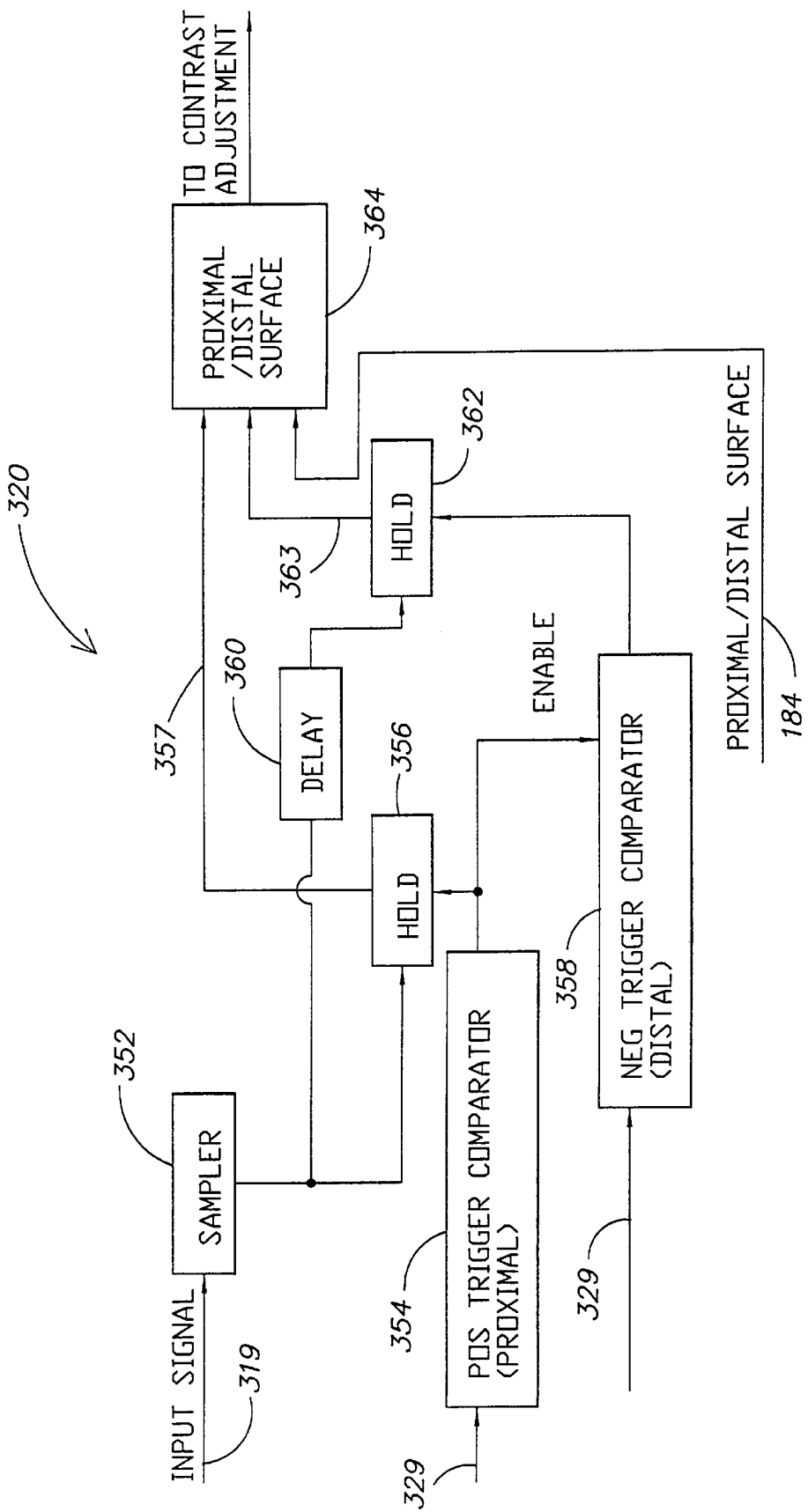
FIG. 5C shows diagrammatically a gated peak detector used in the shown in FIG. 5.

In the preferred embodiment, the TEE imaging system or the transnasal TEE imaging system includes a transmit beamformer, a receive beamformer, an image generator, a surface detector (or a boundary detector), and an image display, all of which are shown diagrammatically in FIGS. 5 through 5C. The system generates several novel orthographic views that utilize planar imaging and projection imaging techniques. The acquisition of the images is first described in connection with FIG. 4. FIG. 4 shows a scanned volume V of data (i.e., an image volume) collected by transducer array 42. Transducer array 42, controlled by a transmit beamformer 200A (described in connection with FIG. 5B), emits ultrasound lines over an azimuthal angular range for a selected elevation angle $\Phi$. Transducer array 42 detects echoes timed by a receive beamformer 200B (described in connection with FIG. 5B) over a selected scan range (R) and an azimuthal angular range ($\theta=\pm45°$) to acquire ultrasound data for one image plane, e.g., $S_0$, shown in FIG. 4. To image the tissue volume V, the imaging system collects data over several image planes (called 2D slices or image sectors) labeled as $S_{-1}$, $S_{-2}$, $S_{-3}$, $S_0$, $S_1$, $S_2$ and $S_3$, distributed over an elevational angular range ($\Phi\pm30°$).

Figure 4A:
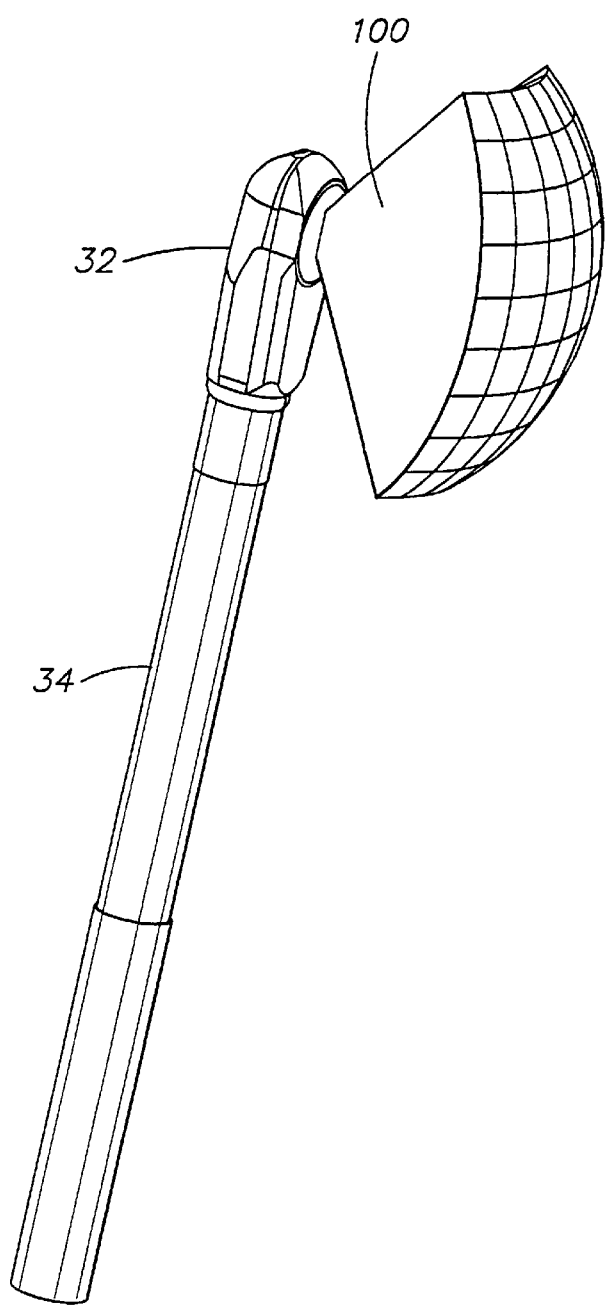
FIGS. 4A, 4B, 4C, 4D and 4E show different orientations of the scanned volumes generated by articulating the distal part as described in connection with FIGS. 3 through 3B.
Figure 4B:
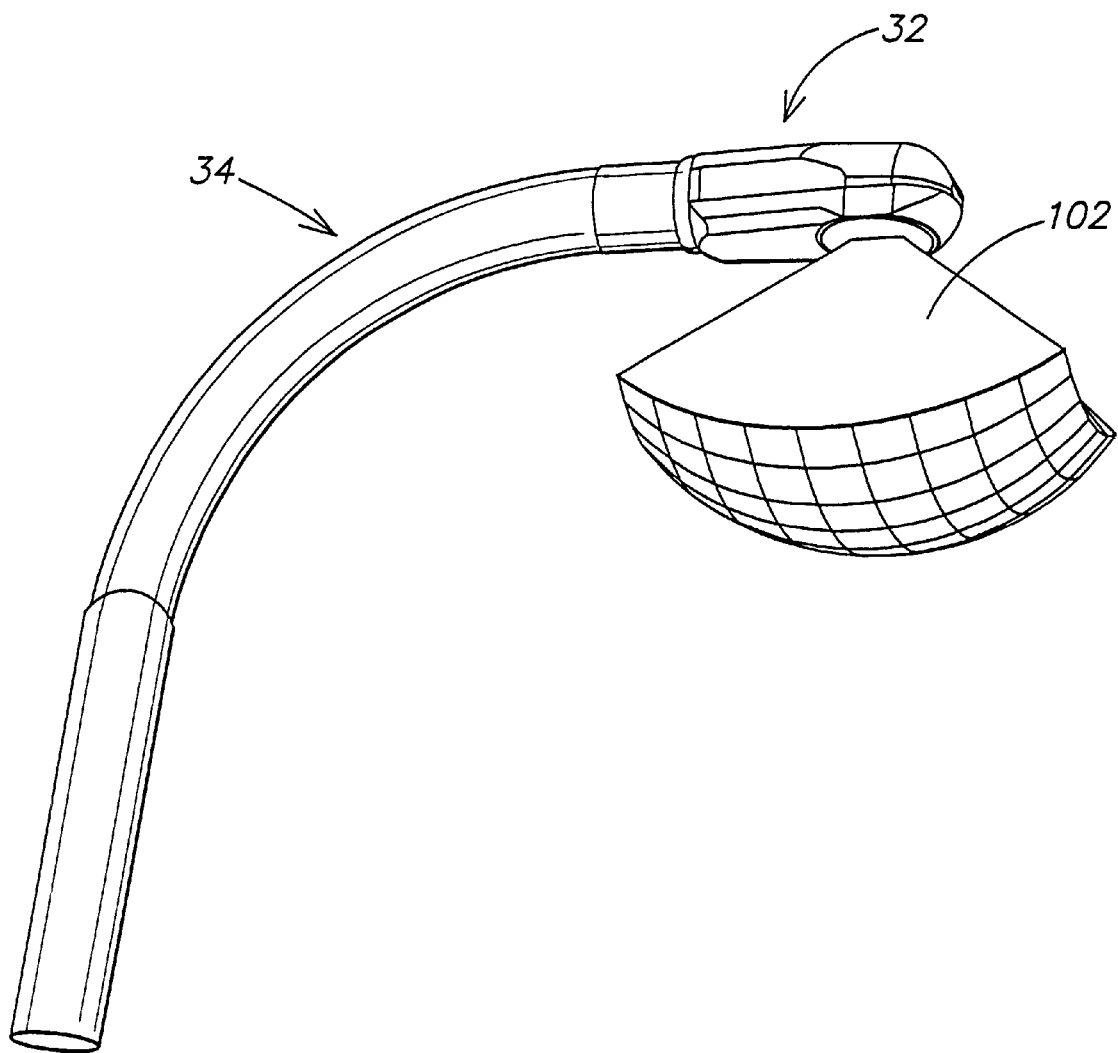
Figure 4C:
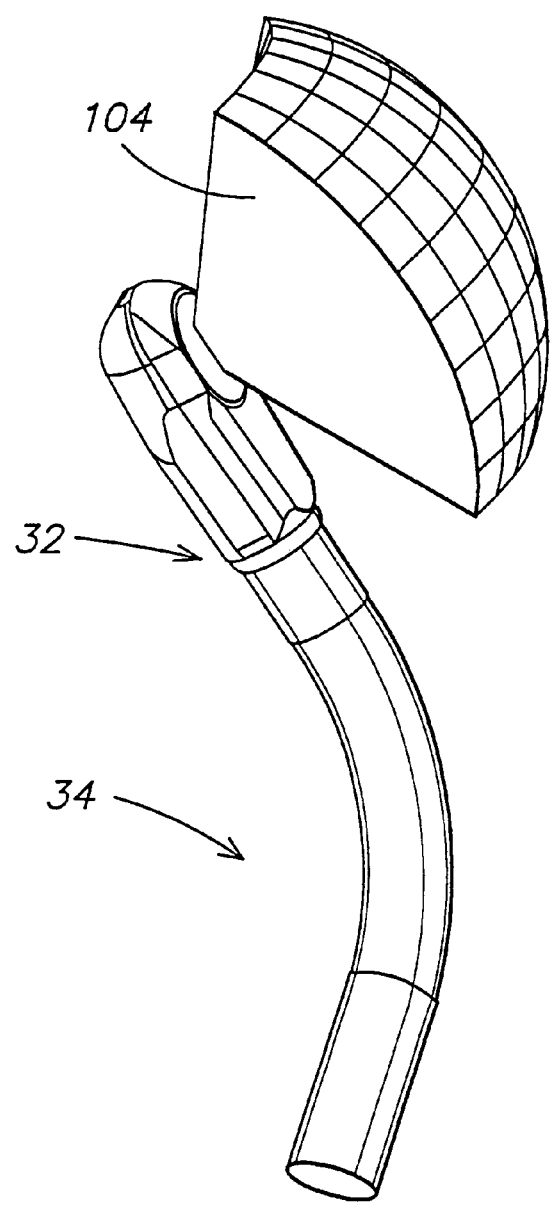
Figure 4D:
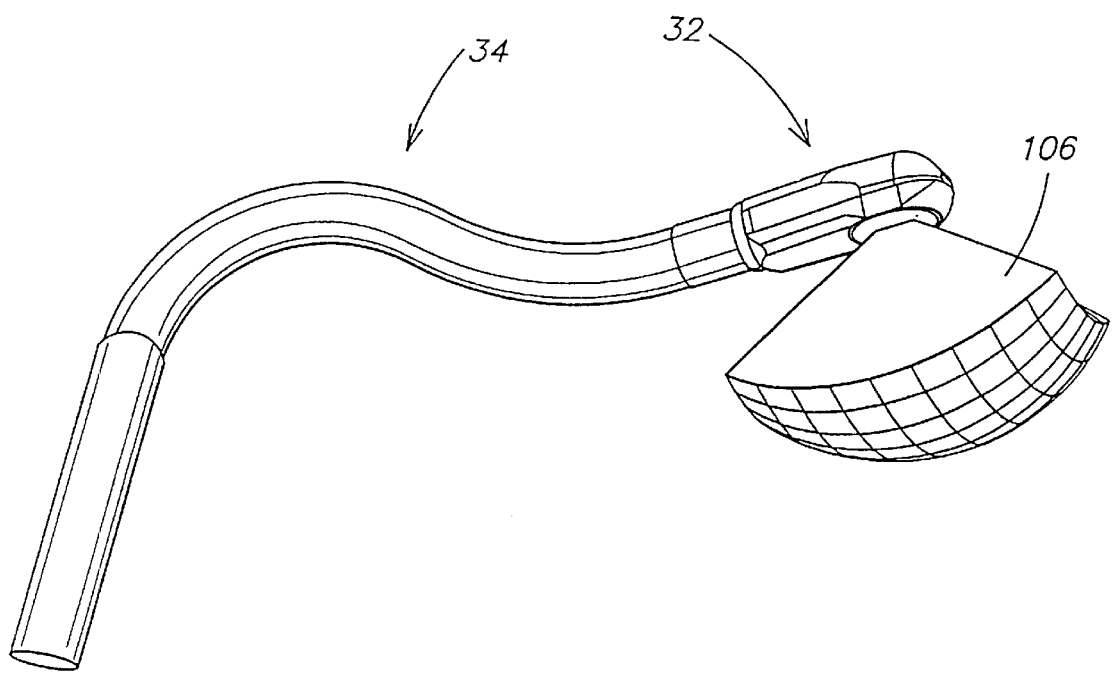
Figure 4E:
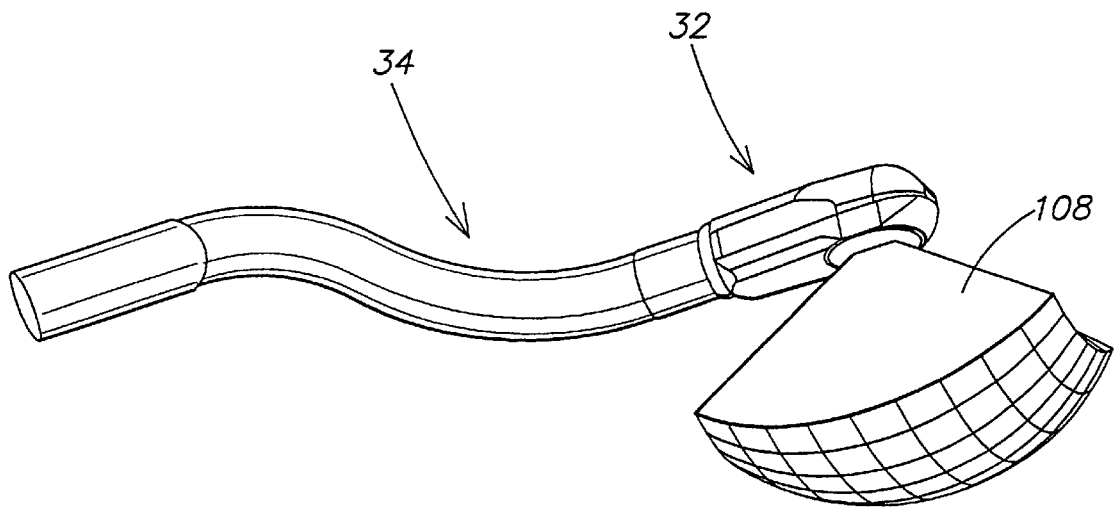

FIGS. 4A through 4E show examples of different orientations of the scanned volumes collected by imaging probe 12 having the probe articulations described in connection with FIGS. 3 through 3C. Specifically, FIG. 4A shows an imaging volume 100 collected by imaging probe 12 having flexible region 34 extended straight. The imaging system collects the echo data over several image planes $S_{-1}$, $S_{-2}$, $S_{-3}$, $S_0$, $S_1$, $S_2$ and $S_3$ described above. FIG. 4B shows a scanned volume 102 collected by the imaging system having flexible region 34 articulated in the form of the in-plane J hook, shown in FIG. 3. The J hook can be articulated in the anterior, as shown in FIG. 4B, direction or the posterior direction and can also be displaced out-of-plane, as described in connection with FIG. 3A. FIG. 4C shows a scanned volume 104 generated by the imaging system with flexible region 34 articulated in the form of the out-of-plane J hook. FIGS. 4D and 4E depict scanned volumes 106 and 108 generated by the imaging system when flexible region 34 is articulated as in-plane and out-of-plan S hooks.

FIGS. 5(1)–5(5), show diagrammatically the imaging system according to a presently preferred embodiment. The entire operation of the imaging system is controlled by a control processor 140, shown in FIG. 5A. Control processor 140 receives input commands from input controls 142 through 167 and provides output control signals 170 through 191. Control processor 140 provides control data to a beamformer 200, and provides image control data to image generator 250, which includes processing and display electronics. Beamformer 200 includes a transmit beamformer 200A and a receive beamformer 200B, shown diagrammatically in FIG. 5B. In general, transmit beamformer 200A and receive beamformer 200B may be analog or digital beamformers as described, for example, in U.S. Pat. Nos. 4,140,022; 5,469,851; or 5,345,426 all of which are incorporated by reference.

According to one embodiment, transducer array 42 is preferably a two-dimensional array of ultrasound transducer elements that can be arranged into groups of elements (i.e., sub-arrays) using electronically-controllable switches. The switches can selectively connect transducer elements together to form sub-arrays having different geometrical arrangements. That is, the two-dimensional array is electronically configurable. The switches also connect the selected configuration to transmit beamformer 200A or receive beamformer 200B shown in FIG. 5B. Each geometrical arrangement of the transducer elements is designed for optimization of the transmitted ultrasound beam or the detected receive beam.

Transducer array 42 may be fabricated using conventional techniques as described, for example, in U.S. Pat. No. 5,267,221 issued Nov. 30, 1993 to Miller et al. The transducer elements may have center-to-center spacings on the order of 100–300 micrometers. The sizes of the transducer elements and the spacings between the transducer elements depend on the transducer ultrasound frequency and the desired image resolution.

Referring to FIG. 5B, the imaging system includes transducer array 42 with designated transmit sub-arrays $43_1$, $43_2, \ldots, 43_M$ and designated receive sub-arrays $44_1, 44_2, \ldots, 44_N$. Transmit sub-arrays $43_1, 43_2, \ldots, 43_M$ are connected to intra-group transmit pre-processors $210_1, 210_2, \ldots, 210_M$, respectively, which in turn are connected to transmit beamformer channels $215_1, 215_2, \ldots, 215_M$. Receive sub-arrays $44_1, 44_2, \ldots, 44_N$ are connected to intra-group receive pre-processors $220_1, 220_2, \ldots, 220_N$, respectively, which in turn are connected to receive beamformer channels $225_1, 225_2, \ldots, 225_N$. Each intra-group transmit pre-processor $210_i$ includes one or more digital pulse generators that provide the transmit pulses and one or more voltage drivers that amplify the transmit pulses to excite the connected transducer elements. Alternatively, each intra-group transmit pre-processor $210_i$ includes a programmable delay line receiving a signal from a conventional transmit beamformer. For example, the transmit outputs from the commercially available ultrasound system HP Sonos 5500 may connected to the intra-group transmit pre-processors $210_i$ instead of the transducer elements done presently for HP Sonos 5500 (both previously manufactured by Hewlett-Packard Company, now Agilent Technologies, Inc., Andover, Mass.).

Each intra-group receive pre-processor $220_i$ may include a summing delay line, or several programmable delay elements connected to a summing element (a summing junction). Each intra-group receive processor $220_i$ delays the individual transducer signals, adds the delayed signals, and provides the summed signal to one receive beamformer channel $225_i$. Alternatively, one intra-group receive processor provides the summed signal to several receive beamformer channels $225_i$ of a parallel receive beamformer. The parallel receive beamformer is constructed to synthesize several receive beams simultaneously. Each intra-group receive pre-processor $220_i$ may also include several summing delay lines (or groups of programmable delay elements with each group connected to a summing junction) for receiving signals from several points simultaneously, as described in detail in U.S. Pat. No. 5,997,479, which is incorporated by reference.

Control processor 140 provides delay commands to transmit beamformer channels $215_1, 215_2, \ldots, 215_M$ via a bus $216_1$ and also provides delay commands to the intra-group transmit pre-processors $210_1, 210_2, \ldots, 210_M$ via a bus 211. The delay data steers and focuses the generated transmit beams over transmit scan lines of a selected transmit pattern, as shown for example in FIGS. 6 through 6C. Control processor 140 also provides delay commands to receive beamformer channels $225_1, 225_2, \ldots, 225_N$ via a bus 226 and delay commands to the intra-group receive pre-processors $220_1, 220_2, \ldots, 220_N$ via a bus 221. The applied relative delays control the steering and focussing of the synthesized receive beams. Each receive beamformer channel $225_i$ includes a variable gain amplifier, which controls gain as a function of received signal depth, and a delay element that delays acoustic data to achieve beam steering and dynamic focusing of the synthesized beam. A summing element 230 receives the outputs from beamformer channels $225_1, 225_2, \ldots, 225_N$ and adds the outputs to provide the resulting beamformer signal to image generator 250, shown in detail in FIG. 5. The beamformer signal represents one receive ultrasound beam synthesized along one receive scan line.

According to another embodiment, transducer array 42 includes a larger number of elements wherein only selected elements are connected to the integrated circuit. Transducer array 42 has the individual transducer elements arranged in rows and columns. The electronically-controllable switches selectively connect the elements adjacent in the rows and columns. Furthermore, the array may also include electronically-controllable switches for selectively connecting adjacent, diagonally-located transducer elements. The selected transducer elements can be connected to the transmit or receive channels of the imaging system such as HP Sonos 5500 or the system described below. A T/R switch connects the same groups of elements alternatively to the transmit or receive channels. The connections may be direct or may be indirect through one or more other transducer elements.

By appropriately connecting the elements into groups and phasing the elements by the transmit beamformer, the generated ultrasound beam is transmitted along a desired scan line and is focused at a desired depth. Various transducer connections are described in U.S. patent application Ser. No. 09/044,464, filed on Mar. 19, 1998, which is incorporated by reference. For example, the transducer elements may be connected in columns together by closing neighboring column switches. Each column is then connected via one selected transducer element of a selected row to a different system channel, as shown in FIG. 5B. The phased transducer elements then form an imaging plane that is perpendicular to the plane of the array and is vertical (i.e., parallel to the selected column). The elevation direction is horizontal, as shown in FIG. 4.

However, the imaging system can generate the scanned volume V by the image planes ($S_{-1}, S_{-2}, S_{-3}, S_0, S_1, S_2$ and $S_3$) oriented arbitrarily relative to the transducer rows and having columns. For example, transducer elements in different rows and columns are interconnected to system channels to provide imaging in a plane that is oriented at an angle with respect to the transducer rows and columns. For example, the transducer elements of neighboring rows and columns are connected to the beamformer in a step-like pattern. This configuration provides the images parallel to a plane that is oriented at about 45 degrees with respect to the column orientation. In another embodiment, the transducer elements are connected the beamformer to form approximately circular contours. This improves the elevation focus control. The acoustic center can be placed on any element that is connected to a system channel. In general, the transducer configurations can be combined with the elevation focus control by determining the appropriate equal delay contours and connecting elements along those contours.

Figure 6:
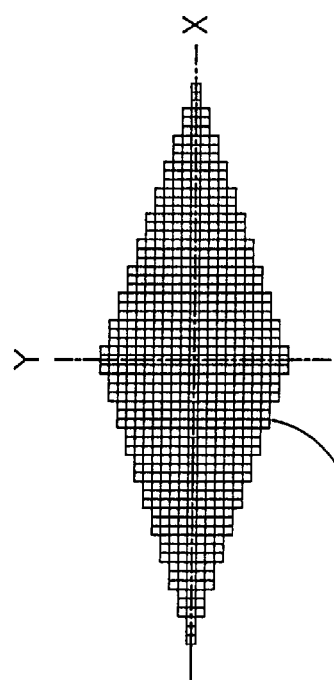
FIGS. 6, 6A, 6B and 6C show various scanning patterns generated by the system of FIG. 5.
Figure 6B:
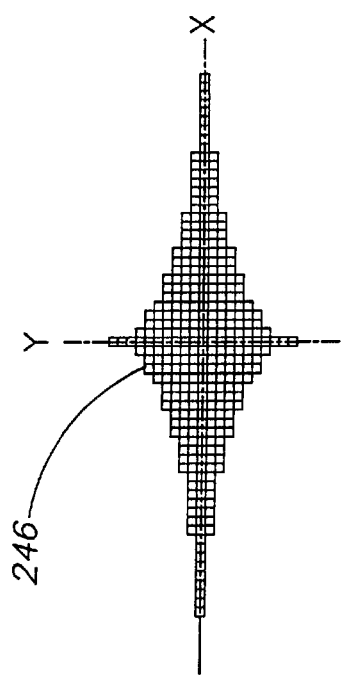
Figure 6A:
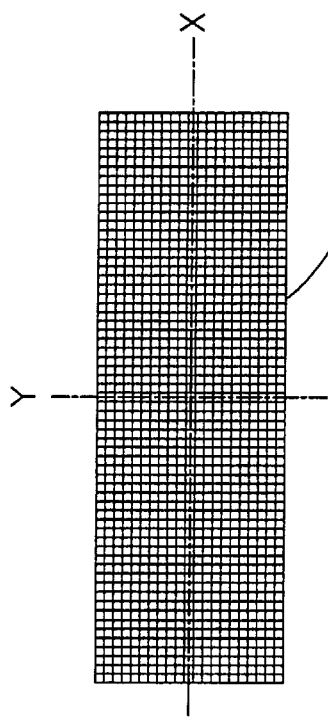
Figure 6C:
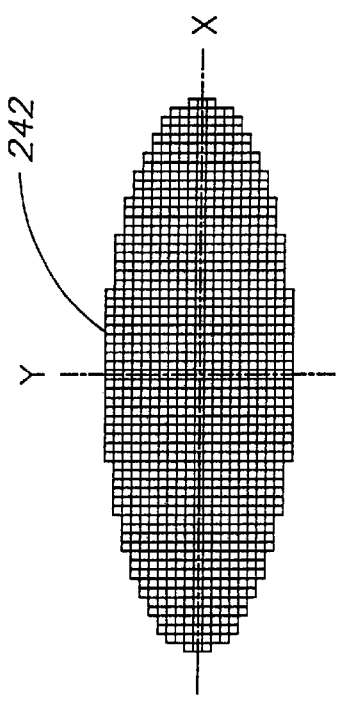
Figure 7:
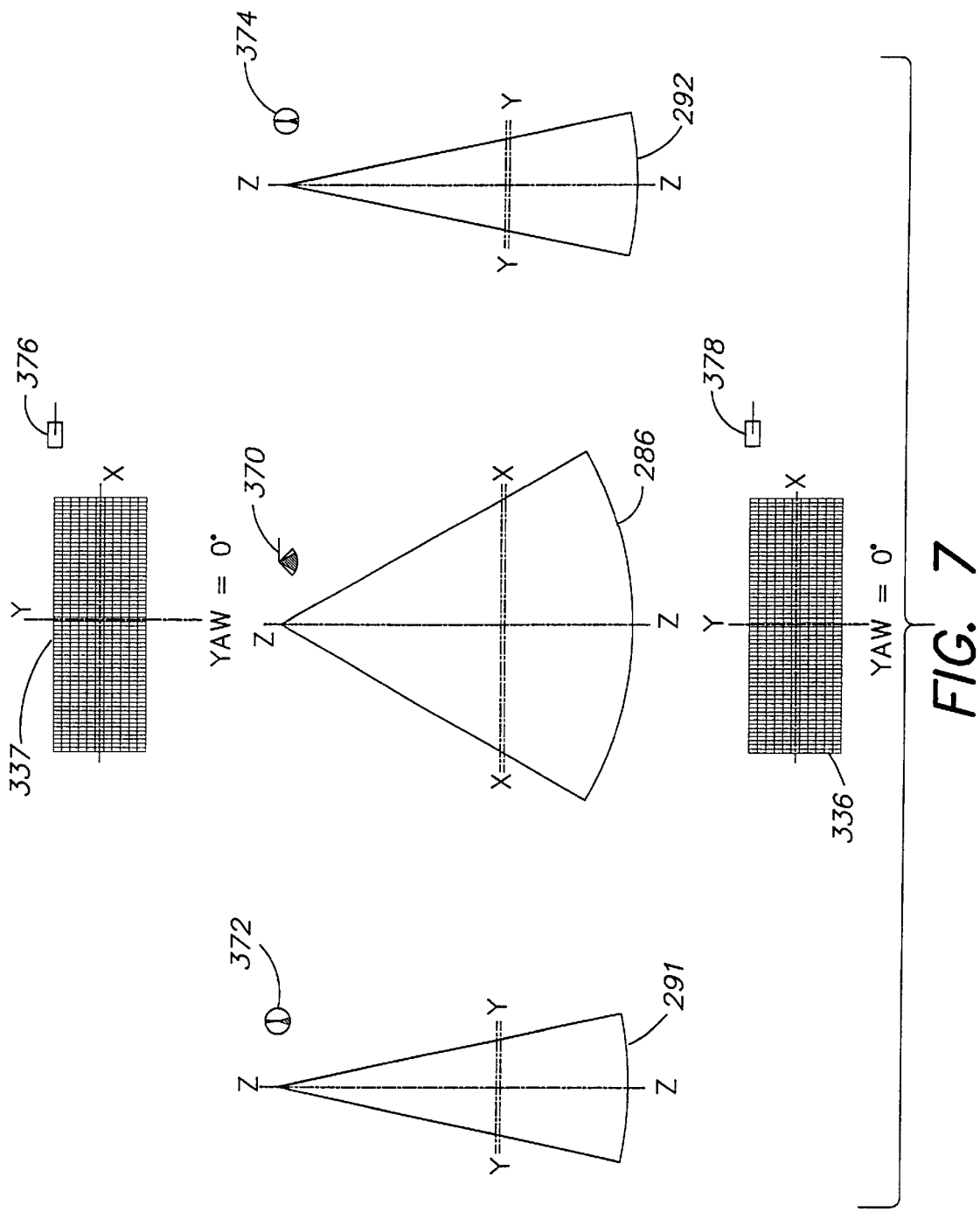
FIG. 7 illustrates five orthographic projection views provided by the ultrasound imaging system of FIG. 1.

The imaging system acquires the echo data over a selected size of the volume V by executing a selected scanning pattern. FIG. 6 shows a 100% rectangular scanning pattern 240 performed, for example, by collecting the echo data over several image planes (2D slices) $S_{-1}, S_{-2}, S_{-3}, S_0, S_1, S_2$ and $S_3$, as described in connection with FIG. 4. However, to reduce the scanning time, the imaging system can perform data scans over a reduced volume centered on the tissue region of interest. For example, FIG. 6A shows an elliptical scanning pattern 242, which includes about 70% of the scan lines used in the rectangular scanning pattern 240, shown in FIG. 6. FIG. 6B shows a diamond-shaped pattern $244_1$ which includes only about 50% of the scan lines, and FIG. 6C shows a star-shaped pattern 246, which includes only about 25% of the scan lines. Referring also to FIG. 7, the imaging system can generate and display several unique views that are within two orthogonal central planes $S_0$ and $L_0$ (FIG. 4) having a zero degree azimuthal and elevational location, respectively. The generated views include projection images that are generated over the region of interest or over the entire area of the 2D slice. Specifically, when the plane $S_0$ (having the elevation angle $\Phi=0°$) is imaged from $y=\infty$ toward $y=0$, it is called a front projection view 286. A rear projection view (not shown in FIG. 7) is imaged from $y=-\infty$ toward $y=0$. The image sectors located at $L_0$ (having the azimuthal angle $\theta=0°$) imaged from $x=\infty$ toward $x=0$ and $x=-\infty$ toward $x=0$ are called a right side projection view 292 and a left side projection view 291, respectively. The imaging system can generate and display a top projection view 337, which is a modified C-scan image of a selected tissue surface imaged from from $z=0$ to $z=\infty$. The location of modified C-scan image can be pre-selected, defined in the plane views (image planes), or defined in the front or side projection views, as shown in FIG. 7. The imaging system also generates and displays a bottom projection view 336, which is a modified C-scan image of the tissue surface imaged from $z=\infty$ to $z=0$. In general, however, the projection direction does not have to be parallel with the x, y or z axes, but may be any direction selected by a clinician.

The imaging system is designed to provide images that are easily understandable to a clinician. As shown in FIG. 7, the image display positions the front projection view (286) in the center, the left side projection view (291) on the left-hand side, and the right side projection view (292) on the right-hand side of the front projection view. Furthermore, the image display displays the top projection view (337) above the front projection view, and the bottom projection view (336) below the front projection view. Next to each view there is a display icon. Display icons 370, 372, 374, 376 and 378 provide the orientation and provide the scan range of the associated views 286, 291, 292, 337 and 336, respectively. The clinician can select and re-select the scan parameters and the display parameters based on the information provided in the individual views and the display icons. The system will then generate new views and the associated display icons, as described below.

Figure 7A:
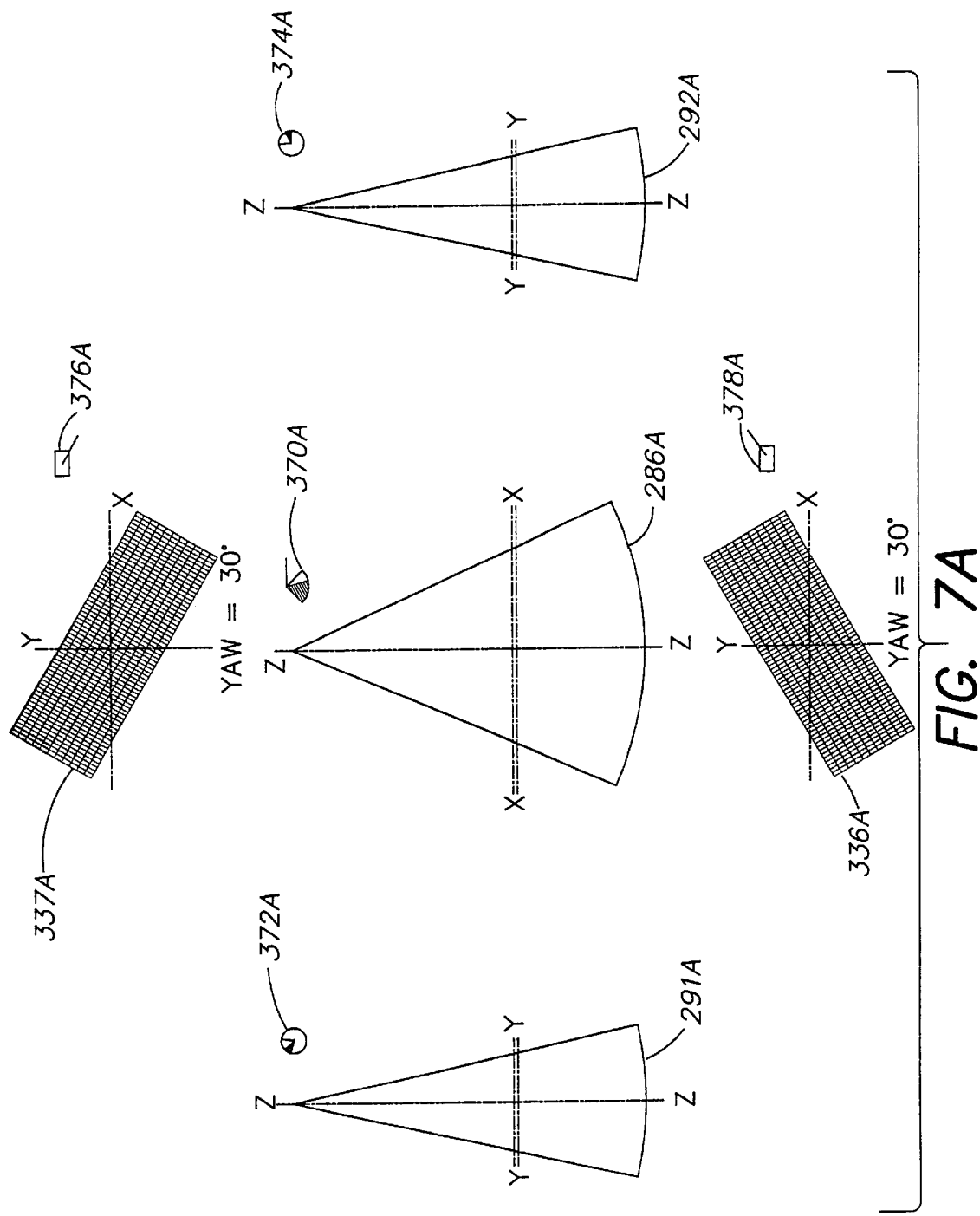
FIG. 7A illustrates the orthographic projection views of FIG. 7 adjusted by changing the yaw angle.

FIG. 7A shows the novel orthographic views of FIG. 7 recalculated for a yaw angle of 30 degrees. The left side projection view 291A and the right side projection view 292A correspond to the left side projection view 291 and the right side projection view 292 (FIG. 7), respectively. The left side view icon 372A, and the right side view icon 374A show the new display regions after recalculating the yaw angle. Similarly, the top view icon 376A and the bottom view icon 378A display the yaw angle to a clinician.

Importantly, the imaging system can generate the projection images over the entire area of a plane view or over a region of interest defined by a clinician after viewing an acquired plane view (i.e., 2D slice image). If the projection images are generated only over the region of interest, than each image includes a projection view within the region of interest and plane view (2D slice) outside the region of interest. Specifically, the right side view includes the right side projection view within the region of interest and a plane view at the plane $L_0$. Similarly, the left side view includes the left side projection view within the region of interest and the plane view at the plane $L_0$. That is, views 291 and 292 (or 291A and 292A) differ only within the region of interest, where the left side projection view and the right side projection view are generated and displayed, and are identical outside the region of interest.

The imaging system initially provides the front view and the side views to a clinician. The imaging system also provides at least one modified C-scan image that is an image of a selected surface perpendicular to the front and side view planes over the scanned volume, V. A clinician can manually select (or the system can select automatically) the surface to be shown in the modified C-scan image. The imaging system generates these orthographic projection views in real time, at a frame rate above 15 Hz (and preferably above 20 Hz, or in the range of about 30 Hz to 100 Hz).

Referring again to FIGS. 5, 5A and 5B, the imaging system includes transmit beamformer 200A and receive beamformer 200B, control processor 140, image generator 250 that includes the surface or boundary detector, and the image display. Control processor 140, shown in FIG. 5A, provides the control data, such as timing 170, a scan line number 171 and a range 175, to beamformer 200 to control scanning within an image sector. In another embodiment, transmit beamformer 200A phases the transmission from the transducer elements to emit the ultrasound beam along several transmit scan lines spaced over a selected angular distribution in a pie-shaped sector. In the receive mode, receive beamformer 200B phases the transducer elements to detect the ultrasound echoes along one or several receive scan lines spaced over a selected angular distribution. The operation of the transmit and receive beamformers connected to a phased array is described, for example, in U.S. Pat. Nos. 4,140,022; 4,893,283; 5,121,361; or 5,469,851.

To define parameters of the B-scan, control processor 140 receives input data defining a sector scan depth 148, a frame rate 150, and an azimuth/elevation scan ratio 152. The sector scan depth defines the scan range (R) over which the echoes are detected, for example, 4 centimeters, 8 centimeters, or 10 centimeters, depending on the location of the transducer array relative to the biological tissue of interest. The clinician can select frame rate 150 depending on the tissue structures of interest. For real-time images of a moving organ, the frame rate has to be at least several frames per second to avoid blurring of the image due to the movement of the tissue. The user also selects azimuth/elevation scan ratio 152, which varies the B-scan from a large azimuth scan (i.e., a large angular range of the scan lines within image sector) of a single sector to a minimum azimuth scan performed over a large number of sectors (i.e., a small angular range for each sector scanned over a large elevation displacement.) Thus, azimuth/elevation scan ratio 152 provides a bottom view image aspect ratio (i.e. x/y dimension) of bottom view 336 and a top view aspect ratio of top view 337 for the C-scan, as shown in FIG. 7.

Depending on the preferred sector scan depth, the frame rate, and the azimuth/elevation scan ratio, control processor 140 calculates the angular spacing between the scan lines and the number of scan lines (171) for each sector. Based on the initial values, processor 140 allocates the largest possible number of scan lines and the largest possible number of sectors. Specifically, processor 140 calculates the angular spacing between the scan sectors, that is, a sector angle (173) and the number of sectors (174). Control processor 140 provides these values to beamformer 200.

Control processor 140 selects the scanning sequence a performed by beamformer 200. The transmit beamformer directs emission of the phased ultrasound beam along the scan lines over the ranges calculated for each sector. For each emitted scan line, the receive beamformer phases the transducer elements to detect the ultrasound echoes along a corresponding receive scan line. Alternatively, the receive beamformer synthesizes the scan data from several receive scan lines that are spaced over a selected angular distribution as is described, for example, in the U.S. Pat. No. 5,976,089, entitled "Increasing the Frame Rate of a Phased Array Imaging System," which is incorporated by reference. The RF data is filtered by a filter with a pass band of as much as 60% around the center frequency of as high as 10 MHz, or preferably a pass band of about 35% around the center frequency in the range of about 5 MHz to 7 MHz.

Control processor 140 receives a time gain compensation (TGC) input 142, a lateral gain compensation (LGC) input 144, and an elevation gain compensation (EGC) input 146 entered by a clinician or stored in a memory. The TGC control adjusts the receive channel gain, usually in discrete steps, as a function of the distance from the transducer array. The TGC control compensates for attenuation of ultrasound waves as they propagate through the medium. The LGC control varies the receive channel gain as a function of the azimuthal displacement of a particular scan line, while the gain along the scan line remains unaffected with the distance from the transducer array. The LGC control is desirable where the ultrasound signal decreases in a particular region due to the anatomical structure of the tissue, or where tissue orientation in the subject results in echo signals having varying brightness. The EGC control varies the receive channel gain as a function of the elevational displacement, i.e., adjusts the gain for a selected scan sector (i.e., scan plan). The user can also re-adjust the TGC, LGC and EGC manually so that the image "looks" better.

Referring to FIGS. 5(1)–5(5), the receive beamformer 200B provides detected RF echo 15 signals to the image generator that includes a time gain compensator (TGC) 262, a lateral gain compensator (LGC) 264, and an elevation gain compensator (EGC) 266, which perform the corrections described above. The EGC 266 provides the compensated data to a B-scan signal processor 272, a C-scan signal processor 315, and boundary detectors 302 and 322.

Alternatively, the TGC 262, the LGC 264 and the EGC 266 are replaced by a rational gain compensation (RGC), which is described in U.S. Pat. No. 5,195,521 and in "Rational Gain Compensation for Attenuation in Cardiac Ultrasonography," *Ultrasonic Imaging*, Vol. 5, pp. 214–228 (1983). The RGC compensates for attenuation while distinguishing between blood and cardiac tissue. The RGC varies the signal gain for blood and cardiac tissue by using a threshold value below which the backscattered signal is defined as "zero." In this case, the backscattered signal is arriving from blood.

Referring still FIGS. 5(1)–5(5), the image generator includes post processors 276 and 318, which receive filtered and compensated data from envelope detectors 274 and 317. Post processors 276 and 318 control the contrast of each data point by mapping the data onto a set of selected curves. After assigning a contrast level to each data point, a scan line buffer may be used to hold temporarily the data for one scan line.

The image generator includes a scan line data volume memory 278 and a boundary data volume memory 280. Scan line data volume memory 278 receives the processed echo data and also receives from processor 140 display line number 172, sector number 174, and range 175. Data volume memory 278 stores the data in a matrix form by assigning a number to each sector and another number to each scan line in the azimuthal direction. The size of the data matrix stored in data volume memory 278 depends upon the acoustic frame rate. Each scan cycle (i.e., acoustic frame) fills the data matrix with the data acquired over the scan volume delineated by the azimuthal range and the elevation range. The scan line number corresponds to the column number in the data volume matrix. The sector number corresponds to the row number in the data volume matrix. The scan range data corresponds to the column height in the data volume matrix. Data volume memory 278 provides its output 279 to view processors 285 and 290.

Boundary data volume memory 280 also receives the processed echo data and data from a majority vote processor 308. Boundary data volume memory 280 also receives from processor 140 display line number 173, sector number 174, range 175 and B-scan surface contrast 179. Data volume memory 280 also stores the data in a matrix form. Data volume memory 280 provides its output 281 to view processors 285 and 290.

Azimuthal view interpolation processor 285 and an elevation view interpolation processor 290 receive data from memory 278 and memory 280 and receive data from B-scan edge indicator 310 and C-scan edge indicator 330. Depending on the view input, interpolation processors 285 and 290 generate the selected front view and the selected side view, respectively. The front and side views are provided to a display plane memory 300 which in turn provides a video signal 350 to a video display. Based on the B-scan data, a clinician can select a region that includes a selected tissue region. The clinician selects the tissue of interest either by setting range gates or by drawing a region of interest (ROI) around the imaged tissue.

The imaging system is designed for automatic operation or interaction with a clinician. A clinician can outline the region of interest by looking at the front plane view or the side plane view (i.e., the B-scan images). Based on the outline (or another input), control processor 140 transforms an ROI perimeter input 153 into a range 175, ROI markers and gates 176. They can be displayed on the video display to outline a region. They are also provided to boundary detector 302 and boundary detector 322 to perform surface (boundary) detection in response to echoes from points within the ROI. Thus, the surface detector (i.e., at least one of boundary detectors 302 or 322) enables the creation of a projection image region, within the ROI perimeter, and thus the surface detector enables surface visualization.

It is important to note that a tissue surface or a tissue structure usually undulates in and out of a single plane view or even a range of views. Several prior art ultrasound systems can display echo data only in the form of 2D slices or planes. Such plane views may provide images that have a random patchwork of areas. The present invention recognized that a clinician may find it difficult to visualize or understand such plane view images, particularly when the transducer array is not completely aligned with a surface of interest. To eliminate this problem, the present imaging system utilizes planar imaging and projection imaging for visualizing tissue surfaces and in general three-dimensional anatomical structures (including therapy devices, diagnostic devices, corrective devices, stents etc.) inside a patient.

As shown in FIGS. 5(1)–5(5), B-scan boundary detector 302 includes a signal processor 304, a tissue indicator 306, a majority vote processor 308, and an edge indicator 310. U.S. Pat. No. 5,195,521, which is incorporated by reference, discloses a majority vote circuit and circuits for generating the ROI. Control processor 140 provides to boundary detector 302 ROI enable output 176, line number output 171, and sector number output 174. Signal processor 304 derives from the RF data a characteristic sensitive to the difference between the echo from tissue and from blood in order to increase the accuracy of locating the tissue boundary. The characteristic is the amplitude of integrated backscatter from tissue and from blood. Signal processor 304 determines the amplitude of the integrated backscatter and provides it to tissue indicator 306. (Alternatively, tissue indicator 306 may receive the echo RF data directly.)

Tissue indicator 306 outputs a signal that is equal to either one or zero depending on whether the echoes are from tissue or blood. Majority vote processor 308 determines whether the majority of the signals are zero or one for the individual scan lines within a scan sector. That is, majority vote processor 308 produces, at each range, a signal indicative of whether the signal provided by the tissue indicator 306 represents echoes from tissue or blood. Majority vote processor 308 produces this signal for a majority of consecutive scan lines including the line currently being scanned. If indicator 306 outputs for a majority of the lines a signal indicating that reflections at a range are from tissue, majority processor 308 outputs a signal indicative of the fact that the reflections are from tissue. Similarly, if tissue indicator 306 outputs a different signal for a majority of lines, majority vote processor 308 outputs another signal indicative of the fact that the reflections are from blood.

Edge indicator 310 responds to a change in the signal provided by majority vote processor 308 to produce short pulses that are used to form an outline of cavities or ventricles in the image. Specifically, edge indicator 310 includes an edge indicator circuit (disclosed in U.S. Pat. No. 5,195,521) that outputs a high logic level for, e.g., 1 microsecond whenever the output of majority vote processor 308 changes from a high level to a low level and vice versa. The output 312 from edge indicator 310 is provided to processors 285 and 290 for highlighting B-scan borders. Furthermore, the output 309 from majority vote processor 308 is provided to boundary data volume memory 280 as described above.

C-scan boundary detector 322 operates similarly as B-scan boundary detector 302. C-scan boundary detector 322 includes a signal processor 324, a tissue indicator 326, a majority vote processor 328, and an edge indicator 330. Control processor 140 provides to boundary detector 322 a range gate enable output 177, line number output 171, and sector number output 174. Signal processor 324 derives from the RF data the amplitude of integrated backscatter from tissue and from blood and provides it to tissue indicator 326. Tissue indicator 326 outputs a signal that is equal to either one or zero depending on whether the echoes are from tissue or blood. Majority vote processor 328 determines whether the majority of the signals are zero or one for the individual scan lines within a scan sector. That is, majority vote processor 328 produces, at each range, a signal indicative of whether the signal provided by the tissue indicator 326 represents echoes from tissue or blood.

As described for edge indicator 310, edge indicator 330 responds to a change in the signal provided by majority vote processor 328 to produce short pulses that are used to form an outline of cavities or ventricles in the image. Specifically, edge indicator 330 outputs a high logic level whenever the output of majority vote processor 328 changes from a high level to a low level and vice versa; that is, the detected echoes change from tissue to blood and vice versa. The output 332 from edge indicator 330 is provided to processors 285 and 290 for highlighting C-scan borders. Furthermore, the output 329 from majority vote processor 328 is provided to a gated peak detector 320.

Referring to FIG. 5C, gated peak detector 320 provides the C-scan data that follow a selected tissue surface located within the selected ROI or range. A sampler 352 receives output 319 from post-processor 318 and provides the sampled data to a hold circuit 356 and to a delay circuit 360. Furthermore, the output 329 of majority vote processor 328 is provided to a positive trigger comparator 354 and to a negative trigger comparator 358. When majority vote processor 328 detects the proximal tissue surface, positive trigger comparator 354 provides an enable signal to hold circuit 356, which in turn provides its output 357 to a proximal/distal surface circuit 364.

A clinician selects the top view or the bottom view using input 162, and control processor 140 provides a proximal/distal surface output 184 to proximal/distal surface circuit 364, which functions as a switch. When majority vote processor 328 is detecting the distal surface, negative trigger comparator 358 provides an enable signal to a hold circuit 362, which in turn provides its output 363 to proximal/distal surface switch 364. Proximal/distal surface switch 364 receives a proximal/distal surface value 184 from control processor 140. Depending on the proximal/distal surface output 184, proximal/distal switch provides signal 357 or signal 363 to a yaw adjustment processor 335 and, in turn, to contrast adjustment processor 340. That is, proximal/distal switch 364 determines whether gated peak detector 320 sends the large value from the positive-going edge of the RF signal, or sends the large value from the negative going edge of the RF signal. In this way, the system generates the data for the top view or the bottom view (both being modified C-scan images).

As described above, gated peak detector 320 selects the proximal or distal surface data from the RF signal and sends it to yaw adjustment processor 335. For a zero degree adjustment (i.e., yaw adjustment output 183 equal to zero), the data is provided unchanged to a contrast adjustment processor 340. Contrast adjustment processor 340 achieves a separate contrast adjustment for the bottom view and the top view (i.e., the two C-scan images). A clinician provides a C-scan contrast input 156, which control processor 140 provides as C-scan output 178. For example, a issue wall may be seen on the front and side views (the B-scan cross-sections) as a white line, but a clinician may want to see it in gray to look for landmarks, lesions or therapy devices in the bottom view. The C-scan contrast creates realistic tissue surface appearance. After the contrast adjustment, contrast adjustment processor 340 provides the contrast adjusted data to a scale adjustment processor 345. Scale adjustment processor 345 maps the contrast adjusted data to the scale used for the front and side views (i.e., B-scan images) and provides the data to video display memory 300.

The ultrasound imaging system 10 provides six degrees of freedom for obtaining and adjusting the image. The electronic adjustment provides three degrees of freedom to obtain a selected view orientation. Three additional degrees of freedom come from the spatial orientation of transducer array 42 relative to a selected tissue structure. Transducer array 42 is oriented by articulating articulation region 34 as shown in FIGS. 3 through 3B. The articulation alters orientation of the scanned volume and thus the orientation of the front, side, and bottom views, as shown in FIGS. 4A through 4E. Image generator 250 provides predictable and easily understandable views of three-dimensional tissue structures.

The orthographic projection views 286, 291 and 292 can be electronically repositioned by providing new input values to control processor 140. After viewing the front view 286 (or the rear view) and the side views 291 or 292, a clinician can electronically change, or reposition the scanned volume V by entering new values for scan sector depth 148, frame rate 150, or azimuth-to-elevation scan ratio 152 to perform another scan. Alternatively, the clinician can re-select the imaged tissue by changing a pitch offset 158 or a roll offset 159 of the new scan. The pitch offset changes the scan lines in the azimuthal direction. The roll offset changes the elevation of a line relative to transducer array 42 and thus changes the position of the individual image sectors, shown in FIG. 4. This way the clinician can direct a scan over a smaller data volume centered on the tissue of interest. By scanning over the smaller volume, the system improves real-time imaging of moving tissue by increasing the frame rate, because it collects a smaller number of data points. Alternatively, the system collects the same number of data points over the smaller volume to increase the resolution.

The imaging system 10 uses several icons to provide understandable images. Referring to FIGS. 5(1)–5(5), 5A(1)–5A(2), and 7, an azimuthal icon generator 289 receives a pitch adjustment 181 and provides data for displaying a front azimuthal icon 370 for the front view (or a rear azimuthal icon for the rear view). An elevation icon generator 299 receives a roll adjustment 182 and provides data for displaying a left elevation icon 372 (shown in FIG. 7) for the left view 291 and a right elevation icon 374 for the right view 292. A yaw icon generator 346 receives a yaw adjustment 183 and provides data for displaying a top icon 376 and a bottom icon 378 showing the yaw orientation (FIG. 7). A clinician uses the icons for better understanding of the images. Furthermore, a clinician uses the icons to steer and direct the acoustic beam to a selected value of interest or to locate and orient the images relative to the orientation of transducer array 42.

The imaging system 10 can also vary electronically the presentation of the orthographic projection views (i.e., the front, rear, side, top, and bottom views). After viewing the front view and the side views (shown in FIG. 7), a clinician can change the orientation of the views by changing a yaw offset 160. Yaw output 183 is provided to processors 285, 290 and 335, which re-calculate the front, side, top and bottom views. The recalculated front view 286A, left side view 291A, right side view 292A, top view 337A and bottom view 336A are shown in FIG. 7A. Furthermore, azimuthal icon generator 289 provides data for displaying front view azimuthal icon 370A, and elevation icon generator 299 provides data for both left view elevation icon 372A and right view elevation icon 374A. Yaw icon generator 346 provides data for displaying both top view icon 376A and bottom view icon 378A.

The yaw adjustment usually requires interpolation to generate new planes of scan lines. These are generated from the nearest set of scan lines using the data volume matrix to create the new data planes (i.e., sectors). This interpolation process uses the same principle as the scan conversion process performed by real-time 2D systems that convert the polar coordinate data into the rectangular coordinate data used for the display (see, e.g., U.S. Pat. No. 4,468,747 or U.S. Pat. No. 5,197,037). Each re-calculated data plane can be stored in a memory associated with processors 285 and 290. The re-calculated data planes are provided to video display plane memory 300 and then to a video monitor by signal 350 (shown in FIG. 5). Scan converters 288 and 298 convert the ultrasound data, acquired in R, theta, into an XY format for both the azimuth and elevation planes. Scan converters 288 and 298 are constructed as described in U.S. Pat. No. 4,468,747; U.S. Pat. No. 4,471,449; or U.S. Pat. No. 5,197,037, or "Ultrasound Imaging: an Overview" and "A Scan Conversion Algorithm for Displaying Ultrasound Images", Hewlett-Packard Journal, October 1983.

Importantly, the entire system provides six degrees of freedom to acquire and generate high quality images. Imaging probe 12 provides three degrees of freedom in positioning transducer array 42 relative to the examined tissue. By articulating, rotating and displacing distal part 30, a clinician maneuvers transducer array 42 to a selected position and orients array 42 relative to the examined tissue. The imaging electronics provides another three degrees of freedom for generating the images by selecting the pitch, roll and yaw values. The display system can generate new (re-oriented) images for different yaw values from the collected scan data stored in the memory. The display format is always predictable from one position (or range of positions) to another and is easily understood by a clinician, as described below. A clinician will understand the three-dimensional structure (in time) due to the novel probe design of the TEE or transnasal TEE probe, and the novel display system that provides anatomically correct orientation of the images. The novel probe design has the centerline of transducer array 42 located at the apex of the pie shaped image shown in FIGS. 9A through 14C.

Figure 8B:
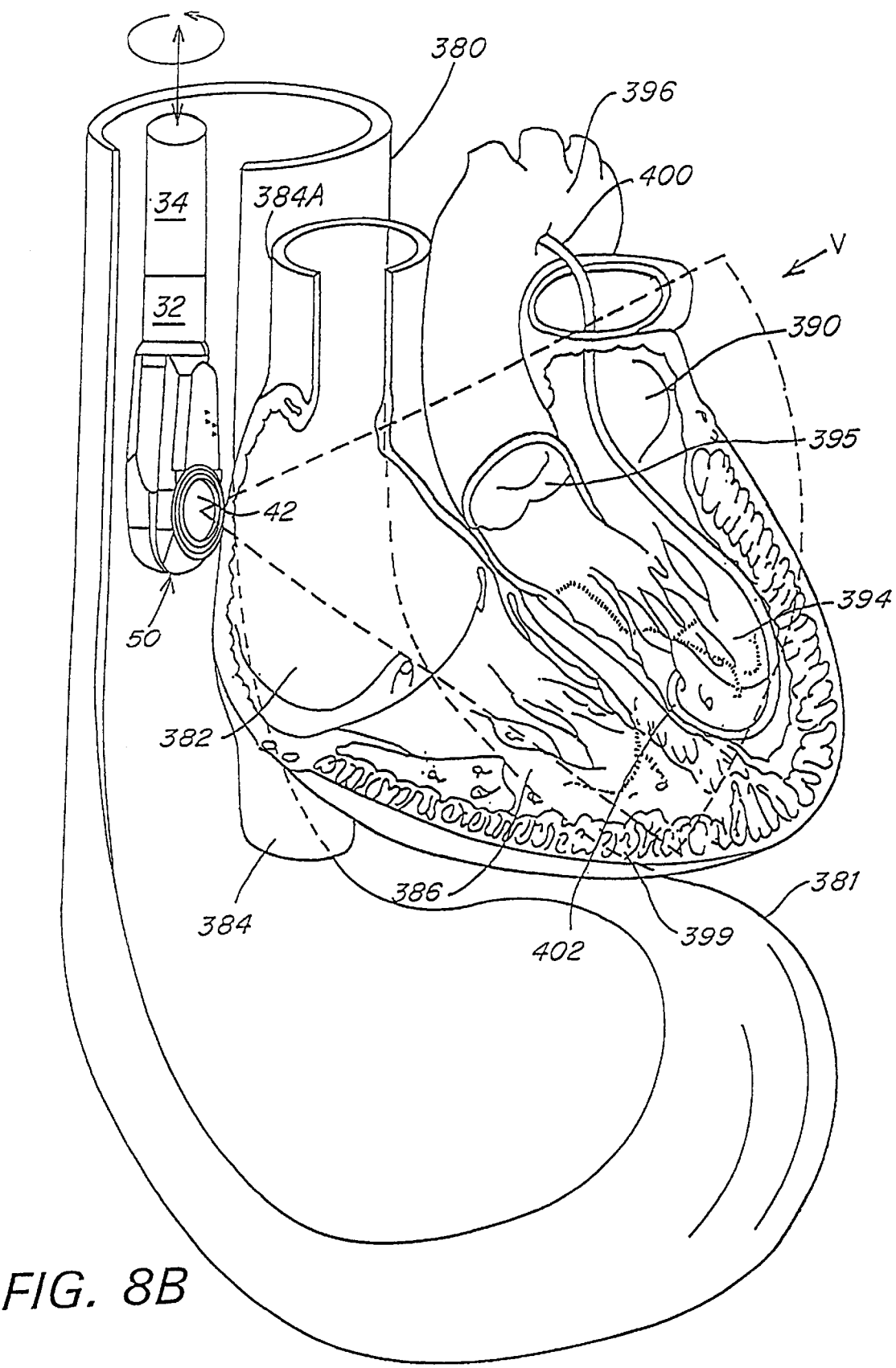
Figure 8C:
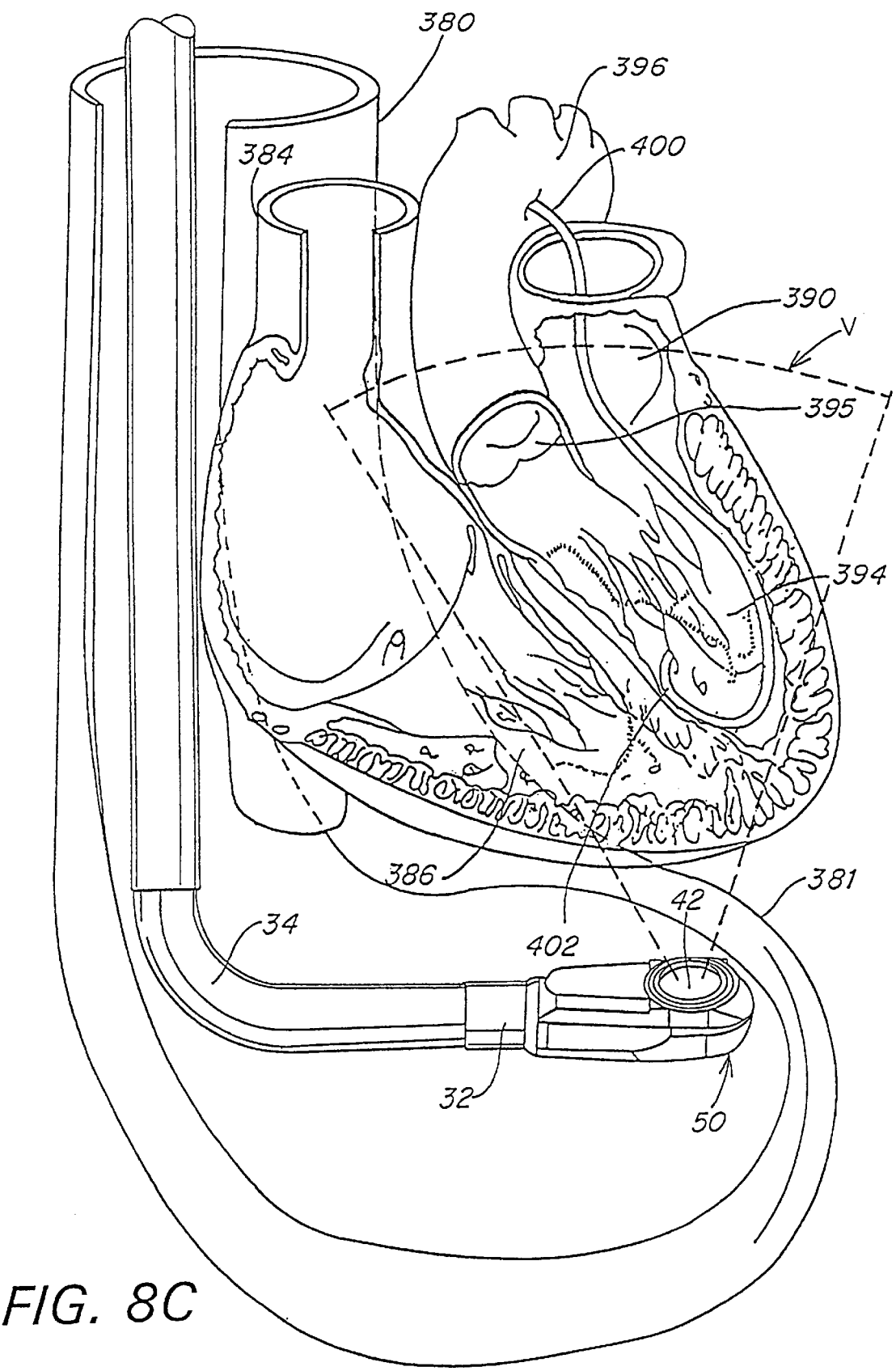

Referring to FIG. 8, prior to collecting the data, a clinician introduces the transesophageal probe with an introducer 135 through the mouth 130, laryngopharynx 132 into the esophagus 380. After moving the probe and the introducer past uvula 133, distal part 50 of the probe is positioned inside the GI track at a desired location. Distal part 50 with transducer array 42 may be positioned inside the esophagus, as shown in FIG. 8B, or the fundus of the stomach, as shown in FIG. 8C. To image the heart, the transmit beamformer focuses the emitted pulses at relatively large depths, and the receive beamformer detects echoes from structures located 10–20 cm away, which is relatively far in range compared to the range used in, for example, an intravascular catheter introduced into the heart.

Alternatively, as shown in FIG. 8A, a clinician introduces the transnasal transesophageal probe with a nasotrumpet introducer 136 into the left nostril 134 (or into the right nostril) and moves them posteriorly in the nasal pharynx, past the uvula 133, into the esophagus 380. Nasotrumpet introducer 136 has a relatively large inner diameter with relatively thin pliable walls. During the introduction procedure, the transnasal TEE probe may support the sheathing of nasotrumpet introducer 136. Both members are curved to the anticipated internal geometry of the patient's nasopharyngeal airways. After introduction, the transnasal TEE probe is moved down in the esophagus 380 and the distal end with the transducer array are positioned at a desired location inside the GI tract.

Similarly as for the TEE imaging probe, the transducer array of the transnasal TEE probe is positioned inside the esophagus (FIG. 8B) or in the fundus of the stomach 381 (FIG. 8C) and oriented to image the tissue of interest. In each case, the imaging system generates several novel types of images. The imaging system is particularly suitable for imaging near tissue using near in range field because of its ability to provide real time imaging of moving organs such as the heart.

Referring to FIGS. 8B and 8C, the imaging probe can image a medical device, such as a balloon catheter or an ablation catheter, introduced into the heart. An ablation catheter 400 (for example, a catheter manufactured by Medtronics, Inc., Sunnyvale, Calif.) is introduced into the left ventricle 394 having its distal part 402 located near or on an interior surface of the myocardium 399. The clinician will understand the three-dimensional structure (in time) due to the novel design of the probe, as sedcribed above. A novel display system provides anatomically correct orientation of the orthographic projection views described in FIGS. 7 and 7A.

FIG. 9A is a cross-sectional view of the human heart along its long axis, and FIG. 9B is a cross-sectional view along the short axis of the heart. FIGS. 9A through 9D are not displayed on the video display of the imaging system, but are provided here for explanation. Both FIGS. 9A and 9B show distal part 30 of probe 12 (shown in FIGS. 1 and 2) located inside into the esophagus 380 (FIG. 8B) and a distal part 402 of an ablation catheter 400 also located inside the right ventricle 386.

Figure 10C:
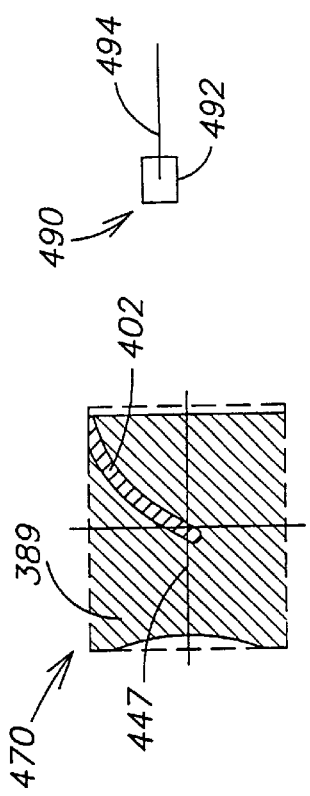
FIGS. 10A, 10B and 10C are orthographic projection views collected by the imaging probe shown in FIGS. 9A and 9B.
Figure 10A:
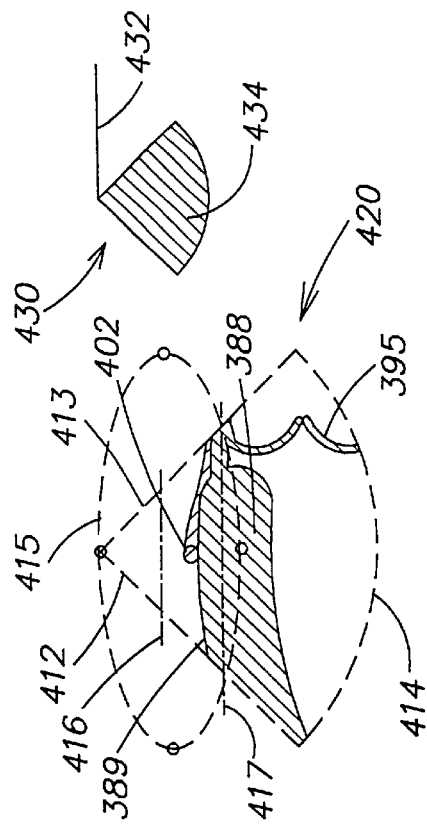
Figure 10B:
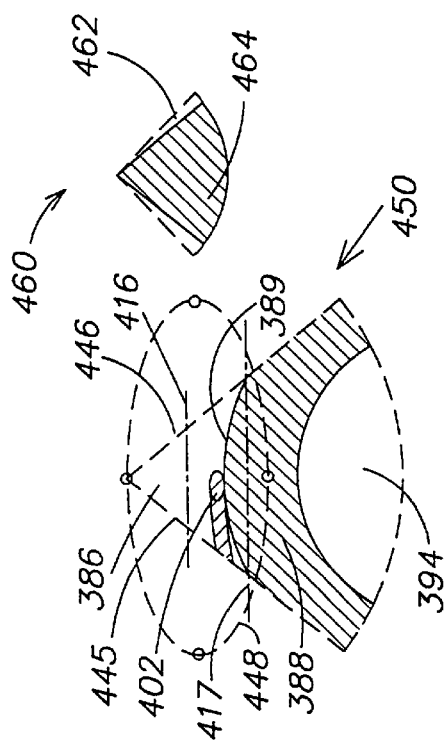

The imaging system uses transducer array 42 to collect the echo data and provides there orthographic views (i.e., views having generally perpendicular orientation with respect to each other), shown in FIGS. 10A, 10B and 10C. The three orthographic views are a front view 420, a left side view 450, and a top view 470, which are generated as plane views with projection views inside the regions of interest or the range of interest. The video display of the imaging system displays each orthographic projection view and an associated icon, as explained in connection with FIGS. 7 and 7A. In the following description, we use the standard definitions of projection views as provided, for example, in *Engineering Drawing and Geometry,* by R. P. Holster and C. H. Springier, John Wiley & Sons, Inc., 1961.

Referring to FIG. 9A, transducer array 42, operating in a phased array mode, collects the echo data over an azimuthal angular range delineated by lines 412 and 413 and a range distance 414. FIG. 10A shows the corresponding front view 420 and a front view icon 430. Front view icon 430 includes an array axis 432 and shows a front view field 434 corresponding to the azimuthal angular range. Array axis 432 shows the longitudinal axis of transducer array 42 for a selected value of yaw adjustment 243 (FIG. 7A). In FIG. 10A, front view 420 shows distal part 402 of ablation catheter 400 positioned on the proximal surface (top surface) 389 of the septum 388, which separates the right ventricle 386 and the left ventricle 394 (shown in FIG. 9A). Front view 420 also partially shows the aortic valve 395 between the left ventricle 394 and the aorta 396. A clinician can set the location of gates 416 and 417 and an ROI marker 415.

Referring to FIGS. 9B and 10B, the imaging system can also generate a left side view 450 by collecting echo data over a selected elevation angular range delineated by lines 445 and 446 and an ROI marker 448. Transducer array 42 (FIG. 9A) collects echo data over a selected number of image sectors, wherein a line 447 indicates the location of the front view plane. Left side view 450 displays a portion of the left ventricle 394, the right ventricle 386, the septum 388, and distal part 402 of catheter 400, located on the right ventricular surface 389 of the septum 388. Referring still to FIG. 10B, left side view icon 460 shows an available side view field 462 and an elevation angular range 464, over which the image sectors were acquired.

FIGS. 9C and 9D are projection views of the human heart. FIG. 9D shows a cut-away top view displaying distal part 402 of the ablation catheter and the surface 389 of the septum 388 within the ranges (i.e., gates 416 and 417) defined in FIGS. 9A and 9B. The corresponding FIG. 10C displays a C-scan projection, top view 470, generated from the B-scan data within range gates 416 and 417, and displays a top view icon 490. Top view 470 shows distal part 402 of catheter 400 placed on the proximal surface 389 of the septum 388. Range gates 416 and 417 and angular range lines 412, 413, 445, and 446 define the area of top view 470. The area of top view 470 is not identical to the shaded area due to the curvature of the proximal surface 389 of the septum 388. FIG. 1C also displays top view icon 490, which includes a rectangular array 492 and an array axis 494. The angle of axis 494 relative to the side of rectangular area 492 indicates the yaw angle of top view 470, wherein the yaw angle is zero in this case.

Figure 11D:
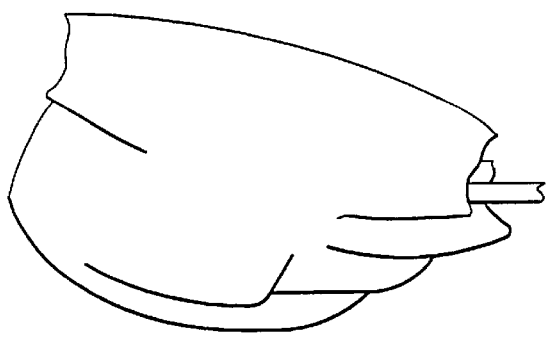
FIG. 11D is a projection view of the human heart.
Figure 11B:
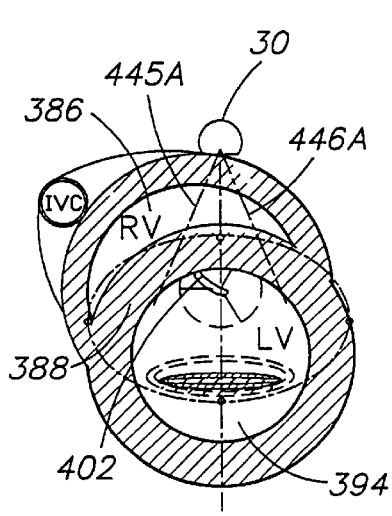
FIGS. 11A and 11B are cross-sectional views of the human heart with the imaging probe inserted in the esophagus and an ablation catheter in the left ventricle.
Figure 11A:
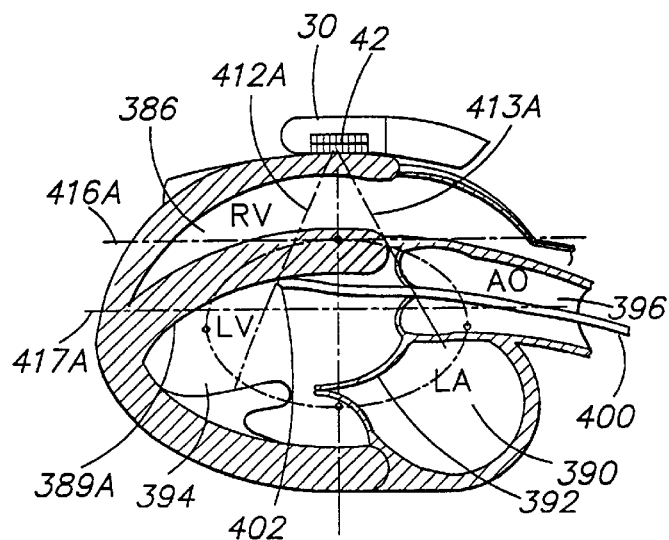

FIGS. 11A and 11B show cross-sectional views of the heart similarly as FIGS. 9A and 9B. The imaging system displays the corresponding front view 420A (shown in FIG. 12A) and left side view 450A (shown in FIG. 12B). However, in the images of FIGS. 12A and 12B, the imaging system uses different values for range gates 416 and 417 and for angular range lines 412, 413, 445 and 446 than in FIGS. 10A and 10B since now distal part 402 of catheter 400 is located now in the left ventricle 394. Furthermore, the imaging system displays a bottom view 500 (shown in FIG. 12C), instead of top view 470 (shown in FIG. 10C), after setting the range gates 416A and 417A in FIGS. 12A and 12B.

FIG. 11A is a cross-sectional view of the heart along the long axis cross-section. The imaging system collects the echo data and generates orthographic front view 420A, shown in FIG. 12A. The system uses a new azimuthal angular range delineated by lines 412A and 413A, which is smaller than the azimuthal angular range used for projection view 420. The smaller azimuthal angular range is selected because the surface of interest is located farther from array 42. In general, in the phased array mode, the imaging system images regions of interest located close to array 42 using larger azimuthal and elevation angular ranges than regions farther away.

Figures 12A, 12B:
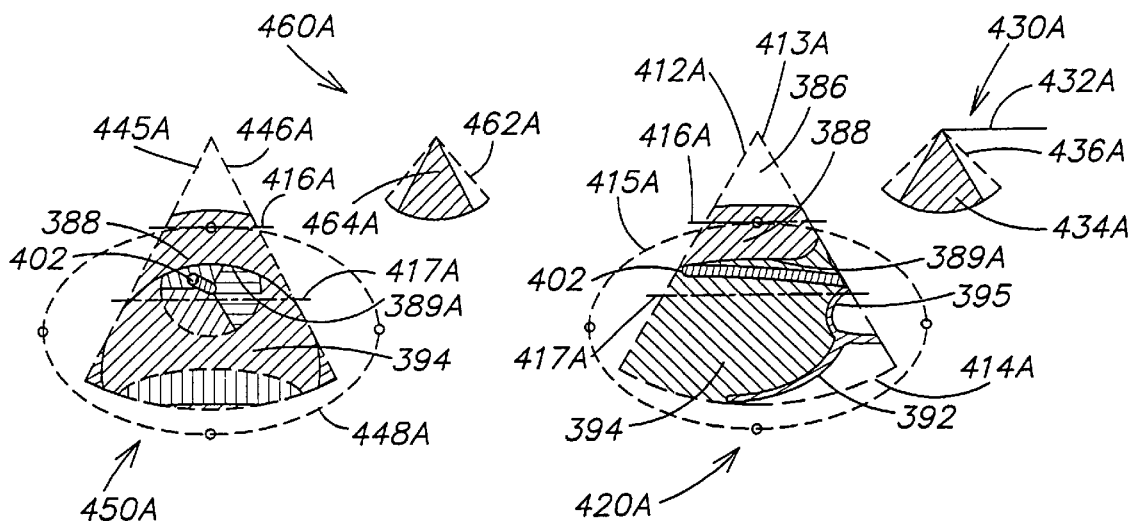
FIGS. 12A, 12B and 12C are orthographic projection views collected by the imaging probe shown in FIGS. 11A and 11B.

Referring to FIG. 12A, front view 420A displays the septum 388, distal part 402 of catheter 400, left ventricle 394, and portions of the mitral valve 392 and aortic valve 395, all located within a range 414A. Front view 420A can display distal part 402 of catheter 400 during, for example, ablation or re-vascularization of the myocardial tissue. FIG. 12A also displays front view icon 430A that includes array axis 432A located at an angle relative to an actual front view field 434A corresponding to the azimuthal angular range defined by lines 412A and 413A. Front view icon 430A includes an available front view field 436A corresponding to a maximum azimuthal angular range. FIG. 11B is a cross-sectional view along the short axis of the heart. FIG. 11B shows distal part 30 of probe 12 (located inside the esophagus 380) and distal part 402 of ablation catheter 400, located inside the left ventricle 394.

FIG. 12B displays left side view 450A and left side view icon 460A. The imaging system generates left side view 450A, which shows a portion of the left ventricle 394, filled with oxygenated blood, and a portion of the right ventricle 386, filled with de-oxygenated blood. Distal part 402 of catheter 400 is located near the distal surface 389A (bottom surface) of the septum 388 within range gates 416A and 417A. Left side view icon 460A shows an available side view field 462A and an actual side view field 464A. Actual side view field 464A displays the elevational angular range of the lines emitted from transducer array 42, which are delineated by lines 445A and 446A. Available side view field 462A corresponds to a maximum elevation angular range.

Figure 11C:
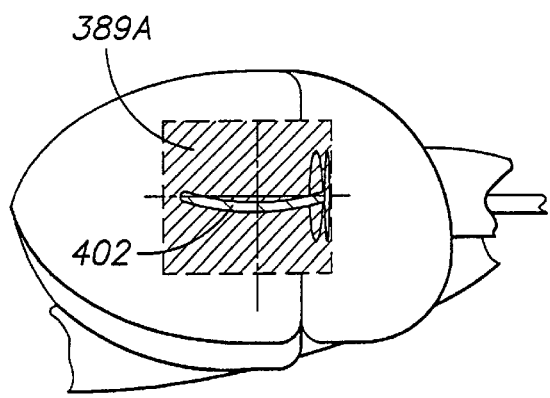
FIG. 11C is a projection view of the human heart including a cut-away bottom view displaying the ablation catheter shown in FIGS. 11A and 11B.
Figure 12C:
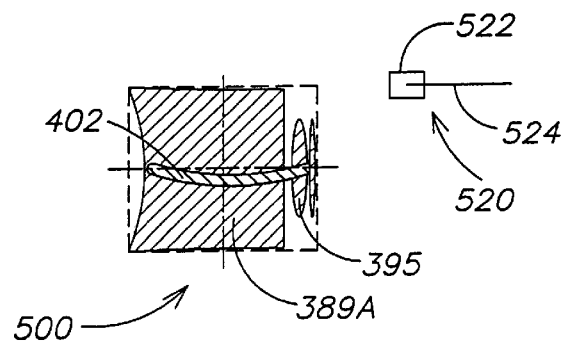

FIGS. 11C and 11D are projection views of the human heart. FIG. 11C shows a cut-away bottom view displaying distal part 402 and bottom surface 389A of the septum 388, both of which are located within the ranges defined in FIGS. 12A and 12B. FIG. 12C displays a C-scan projection, bottom view 500, generated from the B-scan data within range gates 416A and 417A. Bottom view 500 shows distal part 402 placed on the distal surface (left ventricular surface) 389A of the septum 388. Range gates 416A and 417A and angular range lines 412A, 413A, 446A, and 445A define the area of bottom view 500 in FIG. 12C. The area of bottom view 500 is not identical to the shaded area due to the curvature of the proximal surface 389A. FIG. 12C also displays bottom view icon 520, which includes a rectangular array 522 and an array axis 524. The angle of axis 524, relative to the side of rectangular area 522 indicates the yaw angle of top view 500. The yaw angle is zero in this case.

The video display of the imaging system displays the above-described orthographic projection views and the associated icons always at the same location, shown in FIG. 7. The conventional location of each image and icon makes it easier for a clinician to correlate the images to the actual anatomy of the imaged tissue. After providing another value of yaw 160 (FIGS. 5 and 5A), the image generator recalculates all orthographic projection views and displays them at the standard locations. Icon generators 289, 299 and 346 recalculate the data for icons 430A, 460A and 520, all of which are again displayed at the standard locations. The displayed images have anatomically correct orientation.

Figure 13D:
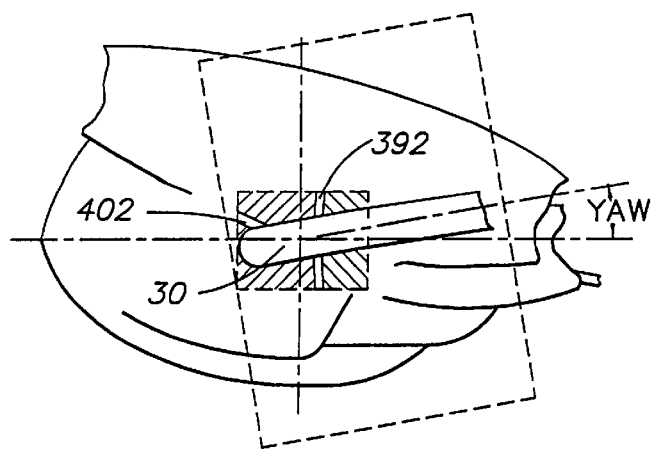
FIG. 13D is a projection view of the human heart including a cut-away top view displaying both the imaging probe and the ablation catheter shown in FIGS. 13A and 13B.
Figure 13B:
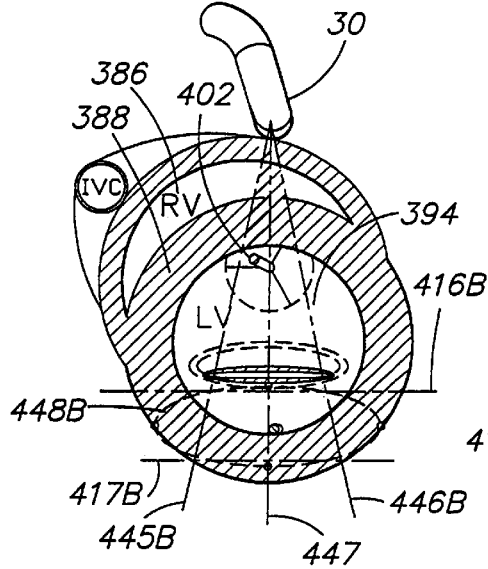
FIGS. 13A and 13B are cross-sectional views of the human heart with the imaging probe inserted in the esophagus and an ablation catheter located in the left ventricle.
Figure 13A:
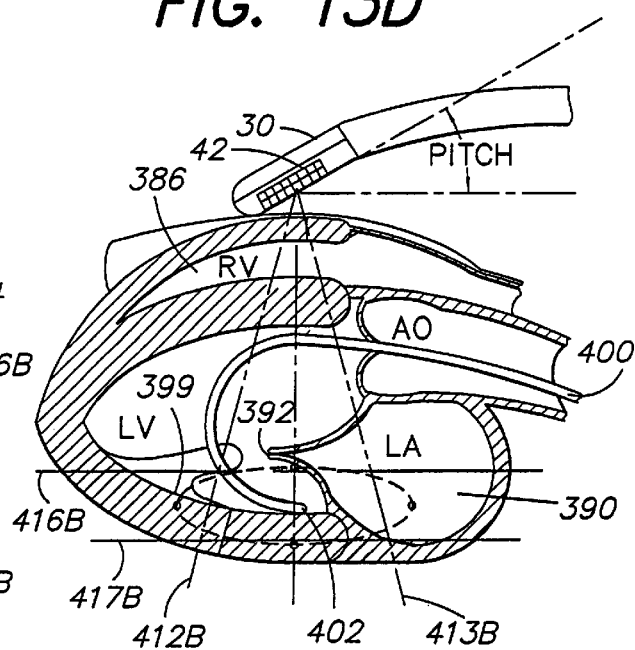

FIGS. 13A and 13B show cross-sectional views of the heart similar to views shown in FIGS. 11A and 11B, respectively. However, in FIGS. 13A and 13B, the imaging system uses range gates 416B and 417B and for angular range lines 412B, 413B, 445B and 446B since distal part 402 of catheter 400 is located now in the left ventricle 394 on a tissue surface 399. The imaging system displays a top view 470B (shown in FIG. 14C), based on the setting of the range gates in FIGS. 14A and 14B.

FIGS. 13A and 13B show distal part 30 of probe 12 located inside the right ventricle 386 and a distal part 402 of ablation catheter 400 also located inside the left ventricle 394. As described above, the imaging system uses transducer array 42 to collect the echo data and generate orthographic projection views shown in FIGS. 14A, 14B and 14C. The video display displays the orthographic projection views and the associated icon at the predetermined locations shown in FIGS. 7 and 7A.

Figure 14C:
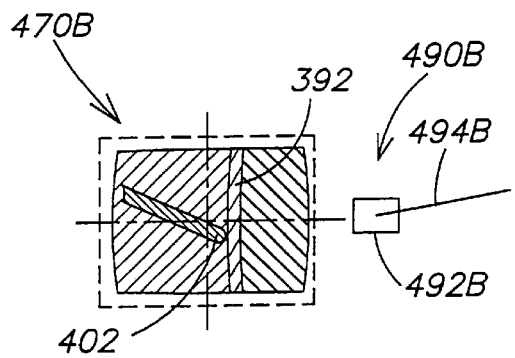
FIGS. 14A, 14B and 14C are orthographic projection views collected by the imaging probe shown in FIGS. 13A and 13B.
Figure 14B:
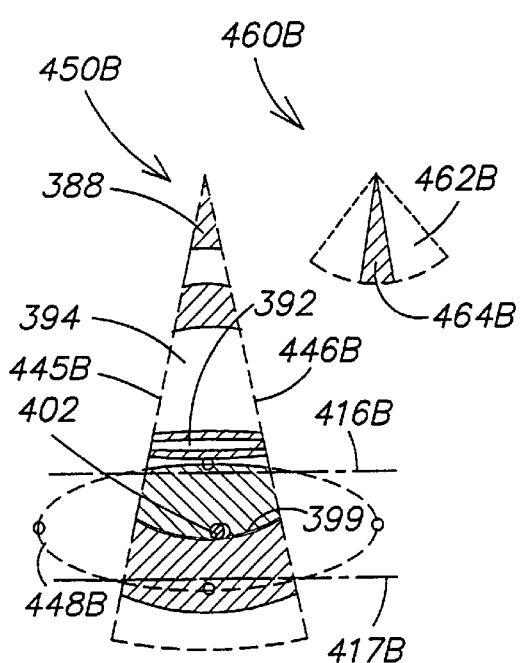
Figure 14A:
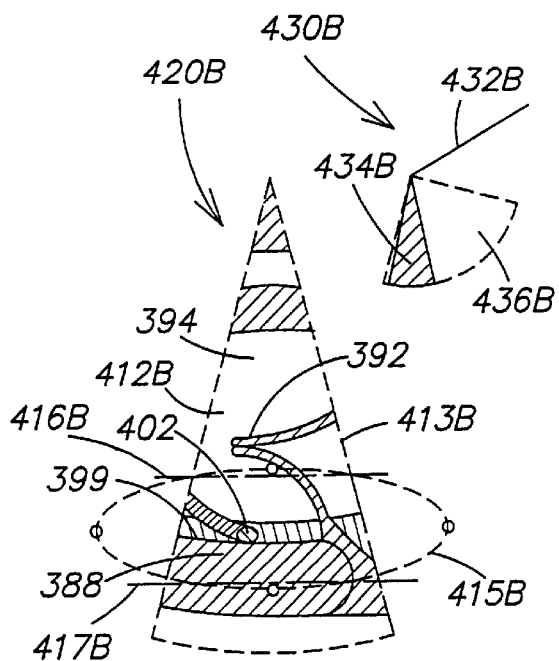

Specifically, FIG. 14A shows a cross-sectional view 420B and a front view icon 430B. Front view 420B shows distal catheter part 402 positioned on tissue surface 399. Front view 420B also shows the mitral valve 392 between the left ventricle 394 and the left atrium 390. A clinician can set the location of gates 416B and 417B and an ROI marker 415B. Front view icon 430B displays an array axis 432B and displays an available front view field 436B and an actual front view field 434B. Actual front view field 434B corresponds to the azimuthal angular range defined by lines 412B and 413B, and available front view field 436B corresponds to a maximum azimuthal angular range. The relationship between actual view field 434B and available view field 436B displays pitch adjustment 181 (FIG. 5A). Array axis 432B relative to actual view field 436B shows a selected value of yaw adjustment 183 (FIG. 5A).

Referring to FIGS. 13B and 14B, the imaging system can also generate a left side view 450B by collecting echo data over a selected elevation angular range delineated by lines 445B and 446B and an ROI marker 448B. Left side view 450B displays a portion of the septum 388, and distal catheter part 402, located on the left ventricular surface 399. Referring still to FIG. 13B, left side view icon 460B displays an available side view field 462B and an actual side view field 464B, which corresponds to the elevation angle over which the image sectors were acquired. The relationship between available view field 462B and actual view field 464B displays roll adjustment 182 (FIG. 5A).

Figure 13C:
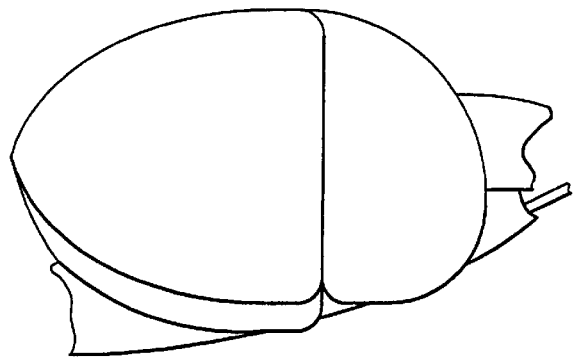
FIG. 13C is a projection view of the human heart.

FIGS. 13C and 13D are projection views of the human heart. FIG. 13D shows a cut-away top view displaying both distal part 30 of probe 12 and distal part 402 of ablation catheter 400 located on the cardiac surface. FIG. 14C displays a C-scan projection, top view 470B, generated from the B-scan data within range gates 416B and 417B, and displays a top view icon 490B. Top view 470B shows distal catheter part 402, located near surface 399, and a portion of the mitral valve 392. Range gates 416B and 417B and angular range lines 412B, 413B, 445B, and 446B define the area of top view 470B. FIG. 14C also displays top view icon 490B, which includes a rectangular array 492B and an array axis 494B. The angle of axis 494B relative to the side of rectangular area 492B indicates the yaw angle of top view 470B.

Additional embodiments are within the following claims:

What is claimed is:

1. A semi-invasive ultrasound imaging system for imaging biological tissue, comprising:
    a probe including an elongated body with a distal end comprising a two-dimensional ultrasound transducer array;
    a transmit beamformer connected to said transducer array and constructed to transmit several ultrasound beams over a selected azimuthal range and a selected elevation range of locations;
    a receive beamformer, connected to said transducer array, constructed to acquire ultrasound data from echoes reflected over a selected tissue volume delineated by said emitted ultrasound beams and a selected sector scan depth and synthesize image data from said acquired ultrasound data; and
    an image generator constructed to receive said image data and generate at least one image of the selected tissue volume that are displayed on an image display.

2. The ultrasound imaging system of claim 1 wherein said image generator is constructed to generate, from said image data, at least two orthographic projection views over the selected tissue volume, and said image display is constructed to display said at least two projection views.

3. The ultrasound imaging system of claim 1 further including a surface detector and a control processor, said surface detector being constructed to receive image parameters from said control processor and generate surface data from the image data; said image generator being constructed to generate from the surface data a projection image for display on said image display.

4. The ultrasound imaging system of claim 3 wherein said surface detector is a B-scan boundary detector and said image generator is constructed to generate, from said image data and said surface data, a plane view including said projection image.

5. The ultrasound imaging system of claim 4 wherein said image generator is constructed to generate, from said image data and said surface data, at least two orthographic projection views each including said plane view and said projection image.

6. The ultrasound imaging system of claim 3 wherein said surface detector is a C-scan boundary detector and said image generator is constructed to generate a C-scan view.

7. The ultrasound imaging system of claim 1 wherein said transducer array and said beamformers are constructed to operate in a phased array mode and acquire said ultrasound data over said selected azimuthal range for several image sectors each having a designated elevation location.

8. The ultrasound imaging system of claim 1 wherein said transducer array includes a plurality of sub-arrays connected to said transmit and receive beamformers.

9. The ultrasound imaging system of claim 1 wherein said probe is a transesophageal probe.

10. The ultrasound imaging system of claim 9 wherein said transesophageal probe includes a locking mechanism co-operatively arranged with an articulation region of said probe and constructed to lock in place said transducer array after orienting said array relative to a tissue region of interest.

11. The ultrasound imaging system of claim 1 wherein said probe is a transnasal transesophageal probe.

12. The ultrasound imaging system of claim 11 wherein said transnasal transesophageal probe includes a locking mechanism co-operatively arranged with an articulation region of said probe and constructed to lock in place said transducer array after orienting said array relative to a tissue region of interest.

13. The ultrasound imaging system of claim 2 further including a control processor constructed and arranged to control said transmission of said ultrasound beams and control said synthesis of said image data based on data provided by a user.

14. The ultrasound imaging system of claim 13 wherein said transducer array includes a plurality of sub-arrays connectable to said transmit and receive beamformers and said control processor is constructed to control arrangement of said sub-arrays for optimizing acquisition of said echo data of said tissue volume.

15. The ultrasound imaging system of claim 13 wherein said control processor constructed and arranged to provide to said transmit beamformer and said receive beamformer scan parameters that include an imaging depth, a frame rate, or an azimuth to elevation scan ratio.

16. The ultrasound imaging system of claim 13 wherein said control processor is constructed to receive input data and provide output data causing said transmit and receive beamformers to change said azimuthal range.

17. The ultrasound imaging system of claim 13 wherein said control processor is constructed to receive input data and provide output data causing said transmit and receive beamformers to change said elevation range.

18. The ultrasound imaging system of claim 13 wherein said control processor is constructed to provide data to image generator for adjusting a yaw of said views by recalculating said orthographic projection views.

19. The ultrasound imaging system of claim 2 wherein said image generator includes at least one view interpolation processor constructed to generate said at least two orthographic projection views, at least one icon generator constructed to generate said at least two icons associated with said at least two orthographic projection views, and at least one boundary detector constructed and arranged to detect a tissue boundary.

20. The ultrasound imaging system of claim 19 wherein the view interpolation processor is arranged to generate a B-scan view and a C-scan view, said C-scan view being generated by receiving C-scan designation information from said B-scan view.

21. The ultrasound imaging system of claim 20 wherein said C-scan designation information includes range gates.

22. The ultrasound imaging system of claim 19 wherein the view interpolation processor is an azimuthal view interpolation processor.

23. The ultrasound imaging system of claim 19 wherein the view interpolation processor is an elevation view interpolation processor.

24. The ultrasound imaging system of claim 19 wherein the view interpolation processor includes a gated peak detector.

25. The ultrasound imaging system of claim 19 wherein said image generator includes a yaw adjustment processor.

26. The ultrasound imaging system of claim 19 wherein said image generator includes a range processor constructed to provide two range cursors for generating a C-scan projection view.

27. The ultrasound imaging system of claim 26 wherein said range processor is arranged to receive a user input defining said two range cursors.

28. The ultrasound imaging system of claim 19 wherein said icon generator constructed to generate an azimuthal icon displaying said azimuthal angular range and displaying a maximum azimuthal angular range.

29. The ultrasound imaging system of claim 19 wherein said icon generator is constructed to generate an elevation icon displaying said elevation angular range and displaying a maximum elevation angular range.

30. A semi-invasive ultrasound imaging method, comprising:

introducing into the esophagus a probe and positioning a two-dimensional ultrasound transducer array at a selected orientation relative to an tissue region of interest;

transmitting ultrasound beams over a plurality of transmit scan lines from said transducer array over a selected azimuthal range and a selected elevation range of locations;

acquiring by said transducer array ultrasound data from echoes reflected from a selected tissue volume delineated by said azimuthal range, said elevation range and a selected sector scan depth and synthesizing image data from said acquired ultrasound data;

generating from said image data at least one image of the selected tissue volume; and displaying said generated image.

31. The imaging method of claim 30 wherein said generating includes creating at least two orthographic projection views over the selected tissue volume.

32. The imaging method of claim 30 further including generating surface data by a surface detector, wherein said generating also includes generating from said surface data a projection image.

33. The imaging method of claim 32 wherein said surface detector is a B-scan boundary detector and said generating from said image data and said surface data includes creating a plane view including said projection image.

34. The imaging method of claim 33 wherein said generating includes creating at least two orthographic projection views each including said plane view and said projection image.

35. The imaging method of claim 32 wherein said surface detector is a C-scan boundary detector and said generating includes creating a C-scan view.

36. The imaging method of claim 30 wherein said transmitting and said acquiring is performed by transmit and receive beamformers constructed to operate in a phased array mode and acquire said ultrasound data over said selected azimuthal range for several image sectors having known elevation locations.

37. The imaging method of claim 30 wherein said generating includes generating at least two orthographic projection views over the tissue volume, and said displaying includes displaying said at least two orthographic projection views.

38. The imaging method of claim 37 further including positioning a surgical instrument at a tissue of interest displayed by said orthographic projection views.

39. The imaging method of claim 38 further including verifying a location of said surgical instrument during surgery based orthographic projection views.

40. The imaging method of claim 37 further including performing said transmitting, said acquiring, said generating, and said displaying of said orthographic projection views while performing surgery with said surgical instrument.

41. The imaging method of claim 37 further including performing said transmitting, said acquiring, said generating, and said displaying of said orthographic projection views after performing surgery with said surgical instrument.

42. The imaging method of claim 33 further including generating by an azimuthal icon generator an azimuthal icon associated with said selected azimuthal range and a maximum azimuthal range.

43. The imaging method of claim 33 further including generating by an elevation icon generator an elevation icon associated with said selected elevation range and a maximum elevation range.

44. The imaging method of claim 37 wherein said generating said several orthographic projection views includes generating a selected C-scan view.

45. The imaging method of claim 44 wherein said generating said selected C-scan view includes providing a C-scan designation for said selected C-scan view.

46. The imaging method of claim 45 wherein said providing said C-scan designation includes defining a bottom view.

47. The imaging method of claim 45 wherein said providing said C-scan designation includes defining a top view.

48. The imaging method of claim 44 wherein generating said C-scan includes detecting a tissue boundary by using a C-scan boundary detector, and selecting ultrasound data for said C-scan by a gated peak detector.

* * * * *